(12) United States Patent
Rottenberg et al.

(10) Patent No.: US 11,266,501 B2
(45) Date of Patent: Mar. 8, 2022

(54) DEVICE AND METHOD FOR CONTROLLING IN-VIVO PRESSURE

(71) Applicant: V-Wave Ltd., Caesarea (IL)

(72) Inventors: Dan Rottenberg, Haifa (IL); Ori J. Braun, Palo Alto, CA (US); Avraham Aba Zakay, Zichron-Yaakov (IL); Ascher Shmulewitz, Tel-Aviv (IL); Yoram Rozy, Caesarea (IL); Gad Keren, Kiryat-Ono (IL)

(73) Assignee: V-Wave Ltd., Caesarea (IL)

( * ) Notice: Subject to any disclaimer, the term of this patent is extended or adjusted under 35 U.S.C. 154(b) by 179 days.

(21) Appl. No.: 16/672,420

(22) Filed: Nov. 1, 2019

(65) Prior Publication Data

US 2020/0060825 A1    Feb. 27, 2020

Related U.S. Application Data

(60) Continuation of application No. 15/668,622, filed on Aug. 3, 2017, now Pat. No. 10,463,490, which is a
(Continued)

(51) Int. Cl.
*A61F 2/24* (2006.01)
*A61B 5/0215* (2006.01)
(Continued)

(52) U.S. Cl.
CPC .......... *A61F 2/2442* (2013.01); *A61B 5/0215* (2013.01); *A61B 17/00234* (2013.01);
(Continued)

(58) Field of Classification Search
CPC .......... A61F 2/24; A61M 27/00; A61B 17/00; A61B 5/0215
See application file for complete search history.

(56) References Cited

U.S. PATENT DOCUMENTS 3,852,334 A   12/1974   Dusza et al.
3,874,388 A   4/1975    King et al.
(Continued)

FOREIGN PATENT DOCUMENTS

AU   2003291117 B2   4/2009
CA   2378920 A1      2/2001
(Continued)

OTHER PUBLICATIONS

U.S. Appl. No. 09/839,643 / U.S. Pat. No. 8,091,556, Apr. 20, 2001 / Jan. 10, 2012.
(Continued)

*Primary Examiner* — Matthew W Schall
(74) *Attorney, Agent, or Firm* — Eversheds Sutherland (US) LLP; Christopher C. Bolten; Nicola A. Pisano

(57) ABSTRACT

A differential pressure regulating device is provided for controlling in-vivo pressure in a body, and in particularly in a heart. The device may include a shunt being positioned between two or more lumens in a body, to enable fluids to flow between the lumens, and an adjustable flow regulation mechanism being configured to selectively cover an opening of the shunt, to regulate the flow of fluid through the shunt in relation to a pressure difference between the body lumens. In some embodiments a control mechanism coupled to the adjustable flow regulation mechanism may be provided, to remotely activate the adjustable flow regulation mechanism.

36 Claims, 22 Drawing Sheets

Related U.S. Application Data division of application No. 13/108,672, filed on May 16, 2011, now Pat. No. 9,724,499, which is a continuation of application No. 10/597,666, filed as application No. PCT/IL2005/000131 on Feb. 3, 2005, now Pat. No. 8,070,708.

(60) Provisional application No. 60/573,378, filed on May 24, 2004, provisional application No. 60/541,267, filed on Feb. 3, 2004.

(51) Int. Cl.
*A61B 17/00* (2006.01)
*A61M 27/00* (2006.01)

(52) U.S. Cl.
CPC .............. *A61F 2/24* (2013.01); *A61F 2/2493* (2013.01); *A61M 27/002* (2013.01); *A61B 2017/00243* (2013.01); *A61B 2017/00252* (2013.01); *A61B 2017/00575* (2013.01); *A61B 2017/00592* (2013.01); *A61B 2017/00606* (2013.01)

(56) References Cited

U.S. PATENT DOCUMENTS

| | | |
|---|---|---|
| 3,952,334 A | 4/1976 | Bokros et al. |
| 4,484,955 A | 11/1984 | Hochstein |
| 4,601,309 A | 7/1986 | Chang |
| 4,617,932 A | 10/1986 | Kornberg |
| 4,662,355 A | 5/1987 | Pieronne et al. |
| 4,665,906 A | 5/1987 | Jervis |
| 4,705,507 A | 11/1987 | Boyles |
| 4,836,204 A | 6/1989 | Landymore et al. |
| 4,979,955 A | 12/1990 | Smith |
| 4,988,339 A | 1/1991 | Vadher |
| 4,995,857 A | 2/1991 | Arnold |
| 5,035,706 A | 7/1991 | Giantureo et al. |
| 5,037,427 A | 8/1991 | Harada et al. |
| 5,089,005 A | 2/1992 | Harada |
| 5,186,431 A | 2/1993 | Tamari |
| 5,197,978 A | 3/1993 | Hess |
| 5,267,940 A | 12/1993 | Moulder |
| 5,290,227 A | 3/1994 | Pasque |
| 5,312,341 A | 5/1994 | Turi |
| 5,326,374 A | 7/1994 | Ilbawi et al. |
| 5,332,402 A | 7/1994 | Teitelbaum |
| 5,334,217 A | 8/1994 | Das |
| 5,378,239 A | 1/1995 | Termin et al. |
| 5,409,019 A | 4/1995 | Wilk |
| 5,429,144 A | 7/1995 | Wilk |
| 5,500,015 A | 3/1996 | Deac |
| 5,531,759 A | 7/1996 | Kensey et al. |
| 5,545,210 A | 8/1996 | Hess et al. |
| 5,556,386 A | 9/1996 | Todd |
| 5,578,008 A | 11/1996 | Hara |
| 5,584,803 A | 12/1996 | Stevens et al. |
| 5,597,377 A | 1/1997 | Aldea |
| 5,645,559 A | 7/1997 | Hachtman et al. |
| 5,655,548 A | 8/1997 | Nelson et al. |
| 5,662,711 A | 9/1997 | Douglas |
| 5,702,412 A | 12/1997 | Popov et al. |
| 5,725,552 A | 3/1998 | Kotula et al. |
| 5,741,324 A | 4/1998 | Glastra |
| 5,749,880 A | 5/1998 | Banas et al. |
| 5,779,716 A | 7/1998 | Cano et al. |
| 5,795,307 A | 8/1998 | Krueger |
| 5,810,836 A | 9/1998 | Hussein et al. |
| 5,824,062 A | 10/1998 | Patke et al. |
| 5,824,071 A | 10/1998 | Nelson et al. |
| 5,846,261 A | 12/1998 | Kotula et al. |
| 5,910,144 A | 6/1999 | Hayashi |
| 5,916,193 A | 6/1999 | Stevens et al. |
| 5,941,850 A | 8/1999 | Shah et al. |
| 5,957,949 A | 9/1999 | Leonhardt et al. |
| 5,990,379 A | 11/1999 | Gregory |
| 6,027,518 A | 2/2000 | Gaber |
| 6,039,755 A | 3/2000 | Edwin et al. |
| 6,039,759 A | 3/2000 | Carpentier et al. |
| 6,086,610 A | 7/2000 | Duerig et al. |
| 6,111,520 A | 8/2000 | Allen et al. |
| 6,117,159 A | 9/2000 | Huebsch et al. |
| 6,120,534 A | 9/2000 | Ruiz |
| 6,124,523 A | 9/2000 | Banas et al. |
| 6,126,686 A | 10/2000 | Badylak et al. |
| 6,165,188 A | 12/2000 | Saadat et al. |
| 6,210,318 B1 | 4/2001 | Lederman |
| 6,214,039 B1 | 4/2001 | Banas et al. |
| 6,217,541 B1 | 4/2001 | Yu |
| 6,221,096 B1 | 4/2001 | Aiba et al. |
| 6,242,762 B1 | 6/2001 | Brown et al. |
| 6,245,099 B1 | 6/2001 | Edwin et al. |
| 6,254,564 B1 | 7/2001 | Wilk et al. |
| 6,260,552 B1 | 7/2001 | Mortier et al. |
| 6,264,684 B1 | 7/2001 | Banas et al. |
| 6,270,515 B1 | 8/2001 | Linden et al. |
| 6,270,526 B1 | 8/2001 | Cox |
| 6,277,078 B1 | 8/2001 | Porat et al. |
| 6,278,379 B1 | 8/2001 | Allen et al. |
| 6,302,892 B1 | 10/2001 | Wilk |
| 6,306,141 B1 | 10/2001 | Jervis |
| 6,328,699 B1 | 12/2001 | Eigler et al. |
| 6,344,022 B1 | 2/2002 | Jarvik |
| 6,358,277 B1 | 3/2002 | Duran |
| 6,391,036 B1 | 5/2002 | Berg et al. |
| 6,398,803 B1 | 6/2002 | Layne et al. |
| 6,406,422 B1 | 6/2002 | Landesberg |
| 6,447,539 B1 | 9/2002 | Nelson et al. |
| 6,451,051 B2 | 9/2002 | Drasler et al. |
| 6,458,153 B1 | 10/2002 | Bailey et al. |
| 6,468,303 B1 | 10/2002 | Amplatz et al. |
| 6,475,136 B1 | 11/2002 | Forsell |
| 6,478,776 B1 | 11/2002 | Rosenman et al. |
| 6,485,507 B1 | 11/2002 | Walak et al. |
| 6,488,702 B1 | 12/2002 | Besselink |
| 6,491,705 B2 | 12/2002 | Gifford et al. |
| 6,527,698 B1 | 3/2003 | Kung et al. |
| 6,544,208 B2 | 4/2003 | Ethier et al. |
| 6,547,814 B2 | 4/2003 | Edwin et al. |
| 6,562,066 B1 | 5/2003 | Martin |
| 6,572,652 B2 | 6/2003 | Shaknovich |
| 6,579,314 B1 | 6/2003 | Lombardi et al. |
| 6,589,198 B1 | 7/2003 | Soltanpour et al. |
| 6,632,169 B2 | 10/2003 | Korakianitis et al. |
| 6,638,303 B1 | 10/2003 | Campbell |
| 6,641,610 B2 | 11/2003 | Wolf et al. |
| 6,652,578 B2 | 11/2003 | Bailey |
| 6,685,664 B2 | 2/2004 | Levin et al. |
| 6,712,836 B1 | 3/2004 | Berg et al. |
| 6,740,115 B2 | 5/2004 | Lombardi et al. |
| 6,758,858 B2 | 7/2004 | McCrea et al. |
| 6,764,507 B2 | 7/2004 | Shanley et al. |
| 6,770,087 B2 | 8/2004 | Layne et al. |
| 6,797,217 B2 | 9/2004 | McCrea et al. |
| 6,890,350 B1 | 5/2005 | Walak et al. |
| 6,970,742 B2 | 11/2005 | Mann et al. |
| 7,001,409 B2 | 2/2006 | Amplatz |
| 7,004,966 B2 | 2/2006 | Edwin et al. |
| 7,025,777 B2 | 4/2006 | Moore |
| 7,060,150 B2 | 6/2006 | Banas et al. |
| 7,083,640 B2 | 8/2006 | Lombardi et al. |
| 7,115,095 B2 | 10/2006 | Eigler et al. |
| 7,118,600 B2 | 10/2006 | Dua et al. |
| 7,137,953 B2 | 11/2006 | Eigler et al. |
| 7,147,604 B1 | 12/2006 | Allen et al. |
| 7,149,587 B2 | 12/2006 | Wardle et al. |
| 7,169,160 B1 | 1/2007 | Middleman et al. |
| 7,169,172 B2 | 1/2007 | Levine et al. |
| 7,195,594 B2 | 3/2007 | Eigler et al. |
| 7,208,010 B2 | 4/2007 | Shanley et al. |
| 7,226,558 B2 | 6/2007 | Nieman et al. |
| 7,245,117 B1 | 7/2007 | Joy et al. |
| 7,294,115 B1 | 11/2007 | Wilk |

(56) References Cited

U.S. PATENT DOCUMENTS

| | | |
|---|---|---|
| 7,306,756 B2 | 12/2007 | Edwin et al. |
| 7,402,899 B1 | 7/2008 | Whiting et al. |
| 7,439,723 B2 | 10/2008 | Allen et al. |
| 7,468,071 B2 | 12/2008 | Edwin et al. |
| 7,483,743 B2 | 1/2009 | Mann et al. |
| 7,498,799 B2 | 3/2009 | Allen et al. |
| 7,509,169 B2 | 3/2009 | Eigler et al. |
| 7,550,978 B2 | 6/2009 | Joy et al. |
| 7,578,899 B2 | 8/2009 | Edwin et al. |
| 7,590,449 B2 | 9/2009 | Mann et al. |
| 7,615,010 B1 | 11/2009 | Najafi et al. |
| 7,621,879 B2 | 11/2009 | Eigler et al. |
| 7,679,355 B2 | 3/2010 | Allen et al. |
| 7,717,854 B2 | 5/2010 | Mann et al. |
| 7,794,473 B2 | 9/2010 | Tessmer et al. |
| 7,839,153 B2 | 11/2010 | Joy et al. |
| 7,842,083 B2 | 11/2010 | Shanley et al. |
| 7,854,172 B2 | 12/2010 | O'Brien et al. |
| 7,862,513 B2 | 1/2011 | Eigler et al. |
| 7,914,639 B2 | 3/2011 | Layne et al. |
| 7,939,000 B2 | 5/2011 | Edwin et al. |
| 7,988,724 B2 | 8/2011 | Salahieh et al. |
| 7,993,383 B2 | 8/2011 | Hartley et al. |
| 8,012,194 B2 | 9/2011 | Edwin et al. |
| 8,016,877 B2 | 9/2011 | Seguin et al. |
| 8,021,420 B2 | 9/2011 | Dolan |
| 8,025,625 B2 | 9/2011 | Allen |
| 8,025,668 B2 | 9/2011 | McCartney |
| 8,043,360 B2 | 10/2011 | McNamara et al. |
| 8,070,708 B2 | 12/2011 | Rottenberg et al. |
| 8,091,556 B2 | 1/2012 | Keren et al. |
| 8,096,959 B2 | 1/2012 | Stewart et al. |
| 8,137,605 B2 | 3/2012 | McCrea et al. |
| 8,142,363 B1 | 3/2012 | Eigler et al. |
| 8,147,545 B2 | 4/2012 | Avior |
| 8,157,852 B2 | 4/2012 | Bloom et al. |
| 8,157,860 B2 | 4/2012 | McNamara et al. |
| 8,157,940 B2 | 4/2012 | Edwin et al. |
| 8,158,041 B2 | 4/2012 | Colone |
| 8,187,321 B2 | 5/2012 | Shanley et al. |
| 8,202,313 B2 | 6/2012 | Shanley et al. |
| 8,206,435 B2 | 6/2012 | Shanley et al. |
| 8,235,916 B2 | 8/2012 | Whiting et al. |
| 8,235,933 B2 | 8/2012 | Keren et al. |
| 8,246,677 B2 | 8/2012 | Ryan |
| 8,287,589 B2 | 10/2012 | Otto et al. |
| 8,298,150 B2 | 10/2012 | Mann et al. |
| 8,298,244 B2 | 10/2012 | Garcia et al. |
| 8,303,511 B2 | 11/2012 | Eigler |
| 8,313,524 B2 | 11/2012 | Edwin et al. |
| 8,328,751 B2 | 12/2012 | Keren et al. |
| 8,337,650 B2 | 12/2012 | Edwin et al. |
| 8,348,996 B2 | 1/2013 | Tuval et al. |
| 8,357,193 B2 | 1/2013 | Phan et al. |
| 8,398,708 B2 | 3/2013 | Meiri et al. |
| 8,460,366 B2 | 6/2013 | Rowe |
| 8,468,667 B2 | 6/2013 | Straubinger et al. |
| 8,480,594 B2 | 7/2013 | Eigler et al. |
| 8,579,966 B2 | 11/2013 | Seguin et al. |
| 8,597,225 B2 | 12/2013 | Kapadia |
| 8,617,337 B2 | 12/2013 | Layne et al. |
| 8,617,441 B2 | 12/2013 | Edwin et al. |
| 8,652,284 B2 | 2/2014 | Bogert et al. |
| 8,665,086 B2 | 3/2014 | Miller et al. |
| 8,696,611 B2 | 4/2014 | Nitzan et al. |
| 8,790,241 B2 | 7/2014 | Edwin et al. |
| 8,882,697 B2 | 11/2014 | Celermajer et al. |
| 8,882,798 B2 | 11/2014 | Schwab et al. |
| 8,911,489 B2 | 12/2014 | Ben-Muvhar |
| 9,005,155 B2 | 4/2015 | Sugimoto |
| 9,034,034 B2 | 5/2015 | Nitzan et al. |
| 9,055,917 B2 | 6/2015 | Mann et al. |
| 9,060,696 B2 | 6/2015 | Eigler et al. |
| 9,067,050 B2 | 6/2015 | Gallagher et al. |
| 9,205,236 B2 | 12/2015 | McNamara et al. |
| 9,220,429 B2 | 12/2015 | Nabutovsky et al. |
| 9,358,371 B2 | 6/2016 | McNamara et al. |
| 9,393,115 B2 | 7/2016 | Tabor et al. |
| 9,456,812 B2 | 10/2016 | Finch et al. |
| 9,622,895 B2 | 4/2017 | Cohen et al. |
| 9,629,715 B2 | 4/2017 | Nitzan et al. |
| 9,681,948 B2 | 6/2017 | Levi et al. |
| 9,707,382 B2 | 7/2017 | Nitzan et al. |
| 9,713,696 B2 | 7/2017 | Yacoby et al. |
| 9,724,499 B2 | 8/2017 | Rottenberg et al. |
| 9,757,107 B2 | 9/2017 | McNamara et al. |
| 9,789,294 B2 | 10/2017 | Taft et al. |
| 9,918,677 B2 | 3/2018 | Eigler et al. |
| 9,943,670 B2 | 4/2018 | Keren et al. |
| 9,980,815 B2 | 5/2018 | Nitzan et al. |
| 10,045,766 B2 | 8/2018 | McNamara et al. |
| 10,047,421 B2 | 8/2018 | Khan et al. |
| 10,076,403 B1 | 9/2018 | Eigler et al. |
| 10,105,103 B2 | 10/2018 | Goldshtein et al. |
| 10,111,741 B2 | 10/2018 | Michalak |
| 10,207,087 B2 | 2/2019 | Keren et al. |
| 10,251,750 B2 | 4/2019 | Eigler et al. |
| 10,299,687 B2 | 5/2019 | Nabutovsky et al. |
| 10,357,320 B2 | 7/2019 | Beira |
| 10,357,357 B2 | 7/2019 | Levi et al. |
| 10,368,981 B2 | 8/2019 | Nitzan et al. |
| 10,463,490 B2 | 11/2019 | Rottenberg et al. |
| 10,478,594 B2 | 11/2019 | Yacoby et al. |
| 10,548,725 B2 | 2/2020 | Alkhatib et al. |
| 10,561,423 B2 | 2/2020 | Sharma |
| 10,639,459 B2 | 5/2020 | Nitzan et al. |
| 10,828,151 B2 | 11/2020 | Nitzan et al. |
| 10,835,394 B2 | 11/2020 | Nae et al. |
| 10,898,698 B1 | 1/2021 | Eigler et al. |
| 10,912,645 B2 | 2/2021 | Rottenberg et al. |
| 10,925,706 B2 | 2/2021 | Eigler et al. |
| 10,940,296 B2 | 3/2021 | Keren |
| 2002/0120277 A1 | 8/2002 | Hauschild et al. |
| 2002/0165479 A1 | 11/2002 | Wilk |
| 2002/0165606 A1 | 11/2002 | Wolf et al. |
| 2002/0169371 A1 | 11/2002 | Gilderdale |
| 2002/0169377 A1 | 11/2002 | Khairkhahan et al. |
| 2002/0173742 A1 | 11/2002 | Keren et al. |
| 2002/0183628 A1 | 12/2002 | Reich et al. |
| 2003/0028213 A1 | 2/2003 | Thill et al. |
| 2003/0100920 A1 | 5/2003 | Akin et al. |
| 2003/0125798 A1 | 7/2003 | Martin |
| 2003/0136417 A1 | 7/2003 | Fonseca et al. |
| 2003/0139819 A1 | 7/2003 | Beer et al. |
| 2003/0176914 A1 | 9/2003 | Rabkin et al. |
| 2003/0209835 A1 | 11/2003 | Chun et al. |
| 2003/0216679 A1 | 11/2003 | Wolf et al. |
| 2003/0216803 A1 | 11/2003 | Ledergerber |
| 2004/0010219 A1 | 1/2004 | McCusker et al. |
| 2004/0016514 A1 | 1/2004 | Nien |
| 2004/0073242 A1 | 4/2004 | Chanduszko |
| 2004/0077988 A1 | 4/2004 | Tweden et al. |
| 2004/0088045 A1 | 5/2004 | Cox |
| 2004/0093075 A1 | 5/2004 | Kuehne |
| 2004/0102797 A1 | 5/2004 | Golden et al. |
| 2004/0116999 A1 | 6/2004 | Ledergerber |
| 2004/0138743 A1 | 7/2004 | Myers et al. |
| 2004/0147869 A1 | 7/2004 | Wolf et al. |
| 2004/0147871 A1 | 7/2004 | Burnett |
| 2004/0147886 A1 | 7/2004 | Bonni |
| 2004/0147969 A1 | 7/2004 | Mann et al. |
| 2004/0162514 A1* | 8/2004 | Alferness ............ A61F 2/2493 604/9 |
| 2004/0193261 A1 | 9/2004 | Berreklouw |
| 2004/0210190 A1 | 10/2004 | Kohler et al. |
| 2004/0210307 A1 | 10/2004 | Khairkhahan |
| 2004/0225352 A1 | 11/2004 | Osborne et al. |
| 2005/0003327 A1 | 1/2005 | Elian et al. |
| 2005/0033327 A1 | 2/2005 | Gainor et al. |
| 2005/0033351 A1 | 2/2005 | Newton |
| 2005/0065589 A1 | 3/2005 | Schneider et al. |
| 2005/0125032 A1 | 6/2005 | Whisenant et al. |
| 2005/0137682 A1 | 6/2005 | Justino |
| 2005/0148925 A1 | 7/2005 | Rottenberg et al. |

(56) References Cited

U.S. PATENT DOCUMENTS

| | | |
|---|---|---|
| 2005/0165344 A1 | 7/2005 | Dobak, III |
| 2005/0182486 A1 | 8/2005 | Gabbay |
| 2005/0283231 A1 | 12/2005 | Haug et al. |
| 2005/0288596 A1 | 12/2005 | Eigler et al. |
| 2005/0288706 A1 | 12/2005 | Widomski et al. |
| 2006/0009800 A1 | 1/2006 | Christianson et al. |
| 2006/0025857 A1 | 2/2006 | Bergheim et al. |
| 2006/0111660 A1 | 5/2006 | Wolf et al. |
| 2006/0116710 A1 | 6/2006 | Corcoran et al. |
| 2006/0122647 A1 | 6/2006 | Callaghan et al. |
| 2006/0167541 A1 | 7/2006 | Lattouf |
| 2006/0184231 A1 | 8/2006 | Rucker |
| 2006/0212110 A1 | 9/2006 | Osborne et al. |
| 2006/0241745 A1 | 10/2006 | Solem |
| 2006/0256611 A1 | 11/2006 | Bednorz et al. |
| 2006/0282157 A1 | 12/2006 | Hill et al. |
| 2007/0010852 A1 | 1/2007 | Blaeser et al. |
| 2007/0021739 A1 | 1/2007 | Weber |
| 2007/0043435 A1 | 2/2007 | Seguin et al. |
| 2007/0129756 A1 | 6/2007 | Abbott et al. |
| 2007/0191863 A1 | 8/2007 | De Juan et al. |
| 2007/0213813 A1 | 9/2007 | Von Segesser et al. |
| 2007/0276413 A1 | 11/2007 | Nobles |
| 2007/0276414 A1 | 11/2007 | Nobles |
| 2007/0282157 A1 | 12/2007 | Rottenberg et al. |
| 2007/0299384 A1 | 12/2007 | Faul et al. |
| 2008/0034836 A1 | 2/2008 | Eigler et al. |
| 2008/0086205 A1 | 4/2008 | Gordy et al. |
| 2008/0125861 A1 | 5/2008 | Webler et al. |
| 2008/0177300 A1 | 7/2008 | Mas et al. |
| 2008/0262602 A1 | 10/2008 | Wilk et al. |
| 2008/0319525 A1 | 12/2008 | Tieu et al. |
| 2009/0030499 A1 | 1/2009 | Bebb et al. |
| 2009/0054976 A1 | 2/2009 | Tuval et al. |
| 2009/0125104 A1 | 5/2009 | Hoffman |
| 2009/0149947 A1 | 6/2009 | Frohwitter |
| 2009/0198315 A1 | 8/2009 | Boudjemline |
| 2009/0276040 A1 | 11/2009 | Rowe et al. |
| 2009/0319037 A1 | 12/2009 | Rowe et al. |
| 2010/0004740 A1 | 1/2010 | Seguin et al. |
| 2010/0022940 A1 | 1/2010 | Thompson |
| 2010/0057192 A1 | 3/2010 | Celermajer |
| 2010/0069836 A1 | 3/2010 | Satake |
| 2010/0070022 A1 | 3/2010 | Kuehling |
| 2010/0081867 A1 | 4/2010 | Fishler et al. |
| 2010/0100167 A1 | 4/2010 | Bortlein et al. |
| 2010/0121434 A1 | 5/2010 | Paul et al. |
| 2010/0179590 A1 | 7/2010 | Fortson |
| 2010/0191326 A1 | 7/2010 | Alkhatib |
| 2010/0249909 A1 | 9/2010 | McNamara et al. |
| 2010/0249910 A1 | 9/2010 | McNamara et al. |
| 2010/0249915 A1 | 9/2010 | Zhang |
| 2010/0256548 A1 | 10/2010 | McNamara et al. |
| 2010/0256753 A1 | 10/2010 | McNamara et al. |
| 2010/0298755 A1 | 11/2010 | McNamara et al. |
| 2011/0022057 A1 | 1/2011 | Eigler et al. |
| 2011/0022157 A1 | 1/2011 | Essinger et al. |
| 2011/0054515 A1 | 3/2011 | Bridgeman et al. |
| 2011/0071623 A1 | 3/2011 | Finch et al. |
| 2011/0071624 A1 | 3/2011 | Finch et al. |
| 2011/0093059 A1 | 4/2011 | Fischell et al. |
| 2011/0152923 A1 | 6/2011 | Fox |
| 2011/0190874 A1 | 8/2011 | Celermajer et al. |
| 2011/0218479 A1 | 9/2011 | Rottenberg et al. |
| 2011/0218480 A1 | 9/2011 | Rottenberg et al. |
| 2011/0218481 A1 | 9/2011 | Rottenberg et al. |
| 2011/0257723 A1 | 10/2011 | McNamara |
| 2011/0264203 A1 | 10/2011 | Dwork et al. |
| 2011/0276086 A1 | 11/2011 | Al-Qbandi et al. |
| 2011/0295182 A1 | 12/2011 | Finch et al. |
| 2011/0295183 A1 | 12/2011 | Finch et al. |
| 2011/0295362 A1 | 12/2011 | Finch et al. |
| 2011/0295366 A1 | 12/2011 | Finch et al. |
| 2011/0306916 A1 | 12/2011 | Nitzan et al. |
| 2011/0319806 A1 | 12/2011 | Wardle |
| 2012/0022633 A1 | 1/2012 | Olson et al. |
| 2012/0035590 A1 | 2/2012 | Whiting et al. |
| 2012/0041422 A1 | 2/2012 | Whiting et al. |
| 2012/0046528 A1 | 2/2012 | Eigler et al. |
| 2012/0046739 A1 | 2/2012 | von Oepen et al. |
| 2012/0053686 A1 | 3/2012 | McNamara et al. |
| 2012/0071918 A1 | 3/2012 | Amin et al. |
| 2012/0130301 A1 | 5/2012 | McNamara et al. |
| 2012/0165928 A1 | 6/2012 | Nitzan et al. |
| 2012/0179172 A1 | 7/2012 | Paul et al. |
| 2012/0190991 A1 | 7/2012 | Bornzin et al. |
| 2012/0265296 A1 | 10/2012 | McNamara et al. |
| 2012/0271398 A1 | 10/2012 | Essinger |
| 2012/0289882 A1 | 11/2012 | McNamara et al. |
| 2012/0290062 A1 | 11/2012 | McNamara et al. |
| 2013/0030521 A1 | 1/2013 | Nitzan et al. |
| 2013/0046373 A1 | 2/2013 | Cartledge et al. |
| 2013/0138145 A1 | 5/2013 | Von Oepen |
| 2013/0178783 A1 | 7/2013 | McNamara et al. |
| 2013/0178784 A1 | 7/2013 | McNamara et al. |
| 2013/0184633 A1 | 7/2013 | McNamara et al. |
| 2013/0184634 A1 | 7/2013 | McNamara et al. |
| 2013/0197423 A1 | 8/2013 | Keren et al. |
| 2013/0197547 A1 | 8/2013 | Fukuoka et al. |
| 2013/0197629 A1 | 8/2013 | Gainor et al. |
| 2013/0204175 A1 | 8/2013 | Sugimoto |
| 2013/0231737 A1 | 9/2013 | McNamara et al. |
| 2013/0261531 A1 | 10/2013 | Gallagher et al. |
| 2013/0281988 A1 | 10/2013 | Magnin et al. |
| 2013/0304192 A1 | 11/2013 | Chanduszko |
| 2014/0012181 A1 | 1/2014 | Sugimoto et al. |
| 2014/0012303 A1 | 1/2014 | Heipl |
| 2014/0012368 A1 | 1/2014 | Sugimoto et al. |
| 2014/0012369 A1 | 1/2014 | Murry et al. |
| 2014/0067037 A1 | 3/2014 | Fargahi |
| 2014/0094904 A1 | 4/2014 | Salahieh et al. |
| 2014/0128795 A1 | 5/2014 | Keren et al. |
| 2014/0128796 A1 | 5/2014 | Keren et al. |
| 2014/0163449 A1 | 6/2014 | Rottenberg et al. |
| 2014/0194971 A1 | 7/2014 | McNamara |
| 2014/0213959 A1 | 7/2014 | Nitzan et al. |
| 2014/0222144 A1 | 8/2014 | Eberhardt et al. |
| 2014/0249621 A1 | 9/2014 | Eidenschink |
| 2014/0257167 A1 | 9/2014 | Celermajer |
| 2014/0275916 A1 | 9/2014 | Nabutovsky et al. |
| 2014/0277045 A1 | 9/2014 | Fazio et al. |
| 2014/0277054 A1 | 9/2014 | McNamara et al. |
| 2014/0303710 A1 | 10/2014 | Zhang et al. |
| 2014/0350565 A1 | 11/2014 | Yacoby et al. |
| 2014/0350658 A1 | 11/2014 | Benary et al. |
| 2014/0350661 A1 | 11/2014 | Schaeffer |
| 2014/0350669 A1 | 11/2014 | Gillespie et al. |
| 2014/0357946 A1 | 12/2014 | Golden et al. |
| 2015/0034217 A1 | 2/2015 | Vad |
| 2015/0039084 A1 | 2/2015 | Levi et al. |
| 2015/0066140 A1 | 3/2015 | Quadri et al. |
| 2015/0073539 A1 | 3/2015 | Geiger et al. |
| 2015/0119796 A1 | 4/2015 | Finch |
| 2015/0127093 A1 | 5/2015 | Hosmer et al. |
| 2015/0142049 A1 | 5/2015 | Delgado et al. |
| 2015/0148731 A1 | 5/2015 | McNamara et al. |
| 2015/0148896 A1 | 5/2015 | Karapetian et al. |
| 2015/0157455 A1 | 6/2015 | Hoang et al. |
| 2015/0173897 A1 | 6/2015 | Raanani et al. |
| 2015/0182334 A1 | 7/2015 | Bourang et al. |
| 2015/0190229 A1 | 7/2015 | Seguin |
| 2015/0196383 A1 | 7/2015 | Johnson |
| 2015/0201998 A1 | 7/2015 | Roy et al. |
| 2015/0209143 A1 | 7/2015 | Duffy et al. |
| 2015/0230924 A1 | 8/2015 | Miller et al. |
| 2015/0238314 A1 | 8/2015 | Bortlein et al. |
| 2015/0245908 A1 | 9/2015 | Nitzan et al. |
| 2015/0272731 A1 | 10/2015 | Racchini et al. |
| 2015/0282790 A1 | 10/2015 | Quinn et al. |
| 2015/0282931 A1 | 10/2015 | Brunnett et al. |
| 2015/0359556 A1 | 12/2015 | Vardi |
| 2016/0007924 A1 | 1/2016 | Eigler et al. |
| 2016/0022423 A1 | 1/2016 | McNamara et al. |
| 2016/0022970 A1 | 1/2016 | Forucci et al. |

(56) References Cited

U.S. PATENT DOCUMENTS

| | | |
|---|---|---|
| 2016/0073907 A1 | 3/2016 | Nabutovsky et al. |
| 2016/0120550 A1 | 5/2016 | McNamara et al. |
| 2016/0129260 A1 | 5/2016 | Mann et al. |
| 2016/0157862 A1 | 6/2016 | Hernandez et al. |
| 2016/0166381 A1 | 6/2016 | Sugimoto et al. |
| 2016/0184561 A9 | 6/2016 | McNamara et al. |
| 2016/0206423 A1 | 7/2016 | O'Connor et al. |
| 2016/0213467 A1 | 7/2016 | Backus et al. |
| 2016/0220360 A1 | 8/2016 | Lin et al. |
| 2016/0220365 A1 | 8/2016 | Backus et al. |
| 2016/0262878 A1 | 9/2016 | Backus et al. |
| 2016/0262879 A1 | 9/2016 | Meiri et al. |
| 2016/0287386 A1 | 10/2016 | Alon et al. |
| 2016/0296325 A1 | 10/2016 | Edelman et al. |
| 2016/0361167 A1 | 12/2016 | Tuval et al. |
| 2016/0361184 A1 | 12/2016 | Tabor et al. |
| 2017/0035435 A1 | 2/2017 | Amin et al. |
| 2017/0113026 A1 | 4/2017 | Finch |
| 2017/0128705 A1 | 5/2017 | Forcucci et al. |
| 2017/0135685 A9 | 5/2017 | McNamara et al. |
| 2017/0165532 A1 | 6/2017 | Khan et al. |
| 2017/0216025 A1 | 8/2017 | Nitzan et al. |
| 2017/0224323 A1 | 8/2017 | Rowe et al. |
| 2017/0224444 A1 | 8/2017 | Viecilli et al. |
| 2017/0231766 A1 | 8/2017 | Hariton et al. |
| 2017/0273790 A1 | 9/2017 | Vettukattil et al. |
| 2017/0281339 A1 | 10/2017 | Levi et al. |
| 2017/0312486 A1 | 11/2017 | Nitzan et al. |
| 2017/0319823 A1 | 11/2017 | Yacoby et al. |
| 2017/0325956 A1 | 11/2017 | Rottenberg et al. |
| 2017/0348100 A1 | 12/2017 | Lane et al. |
| 2018/0099128 A9 | 4/2018 | McNamara et al. |
| 2018/0104053 A1 | 4/2018 | Alkhatib et al. |
| 2018/0125630 A1 | 5/2018 | Hynes et al. |
| 2018/0130988 A1 | 5/2018 | Nishikawa et al. |
| 2018/0243071 A1 | 8/2018 | Eigler et al. |
| 2018/0256865 A1 | 9/2018 | Finch et al. |
| 2018/0263766 A1 | 9/2018 | Nitzan et al. |
| 2018/0344994 A1 | 12/2018 | Karavany et al. |
| 2019/0000327 A1 | 1/2019 | Doan et al. |
| 2019/0008628 A1 | 1/2019 | Eigler et al. |
| 2019/0015188 A1 | 1/2019 | Eigler et al. |
| 2019/0021861 A1 | 1/2019 | Finch |
| 2019/0239754 A1 | 8/2019 | Nabutovsky et al. |
| 2019/0328513 A1 | 10/2019 | Levi et al. |
| 2019/0336163 A1 | 11/2019 | McNamara et al. |
| 2020/0078558 A1 | 3/2020 | Yacoby et al. |
| 2020/0085600 A1 | 3/2020 | Schwartz et al. |
| 2020/0197178 A1 | 6/2020 | Vecchio |
| 2020/0261705 A1 | 8/2020 | Nitzan et al. |
| 2020/0315599 A1 | 10/2020 | Nae et al. |
| 2020/0368505 A1 | 11/2020 | Nae et al. |
| 2021/0052378 A1 | 2/2021 | Nitzan et al. |

FOREIGN PATENT DOCUMENTS

| | | |
|---|---|---|
| EP | 2238933 A1 | 10/2010 |
| EP | 2305321 A1 | 4/2011 |
| EP | 1965842 B1 | 11/2011 |
| EP | 3400907 A1 | 11/2018 |
| FR | 2827153 A1 | 1/2003 |
| WO | WO-9531945 A1 | 11/1995 |
| WO | WO-9727898 A1 | 8/1997 |
| WO | WO-99/60941 A1 | 12/1999 |
| WO | WO-00/44311 A2 | 8/2000 |
| WO | WO-0050100 A1 | 8/2000 |
| WO | WO-0110314 A2 | 2/2001 |
| WO | WO-0226281 A1 | 4/2002 |
| WO | WO-02/071974 A2 | 9/2002 |
| WO | WO-02087473 A1 | 11/2002 |
| WO | WO-03/053495 A2 | 7/2003 |
| WO | WO-2005/027752 A1 | 3/2005 |
| WO | WO-2005/074367 A1 | 8/2005 |
| WO | WO-2006/127765 A1 | 11/2006 |
| WO | WO-2007/083288 A2 | 7/2007 |
| WO | WO-2008/055301 A1 | 5/2008 |
| WO | WO-2009/029261 A1 | 3/2009 |
| WO | WO-2010/128501 A1 | 11/2010 |
| WO | WO-2010129089 A2 | 11/2010 |
| WO | WO-2011062858 A1 | 5/2011 |
| WO | WO-2013/096965 A1 | 6/2013 |
| WO | WO-2016/178171 A1 | 11/2016 |
| WO | WO-2017/118920 A1 | 7/2017 |
| WO | WO-2018158747 A1 | 9/2018 |
| WO | WO-2019/015617 A1 | 1/2019 |
| WO | WO-2019/085841 A1 | 5/2019 |
| WO | WO-2019/109013 A1 | 6/2019 |
| WO | WO-2019/142152 | 7/2019 |
| WO | WO-2019/179447 A1 | 9/2019 |
| WO | WO-2019218072 A1 | 11/2019 |

OTHER PUBLICATIONS

U.S. Appl. No. 10/597,666 / U.S. Pat. No. 8,070,708, Jun. 20, 2007 / Dec. 6, 2011.
U.S. Appl. No. 12/223,080 / U.S. Pat. No. 9,681,948, Jul. 16, 2014 / Jun. 20, 2017.
U.S. Appl. No. 13/107,832 / U.S. Pat. No. 8,235,933, May 13, 2011 / Aug. 7, 2012.
U.S. Appl. No. 13/107,843 / U.S. Pat. No. 8,328,751, May 13, 2011 / Dec. 11, 2012.
U.S. Appl. No. 13/108,672 / U.S. Pat. No. 9,724,499, May 16, 2011 / Aug. 8, 2017.
U.S. Appl. No. 13/108,698, filed Jun. 16, 2011.
U.S. Appl. No. 13/108,850, filed May 16, 2011.
U.S. Appl. No. 13/108,880 / U.S. Pat. No. 8,696,611, May 16, 2011 / Apr. 15, 2014.
U.S. Appl. No. 13/193,309 / U.S. Pat. No. 9,629,715, Jul. 28, 2011 / Apr. 25, 2017.
U.S. Appl. No. 13/193,335 / U.S. Pat. No. 9,034,034, Jul. 28, 2011 / May 19, 2015.
U.S. Appl. No. 13/708,794 / U.S. Pat. No. 9,943,670, Dec. 7, 2012 / Apr. 17, 2018.
U.S. Appl. No. 14/154,080 / U.S. Pat. No. 10,207,807, Jan. 13, 2014 / Feb. 19, 2019.
U.S. Appl. No. 14/154,088, filed Jan. 13, 2014.
U.S. Appl. No. 14/154,093, filed Jan. 13, 2014.
U.S. Appl. No. 14/227,982 / U.S. Pat. No. 9,707,382, Mar. 27, 2014 / Jul. 18, 2017.
U.S. Appl. No. 14/282,615 / U.S. Pat. No. 9,713,696, May 20, 2014 / Jul. 25, 2017.
U.S. Appl. No. 14/712,801 / U.S. Pat. No. 9,980,815, May 14, 2015 / May 29, 2018.
U.S. Appl. No. 15/449,834 / U.S. Pat. No. 10,076,403, Mar. 3, 2017 / Sep. 18, 2018.
U.S. Appl. No. 15/492,852 / U.S. Pat. No. 10,368,981, Apr. 20, 2017 / Aug. 6, 2019.
U.S. Appl. No. 15/570,752, filed Oct. 31, 2017.
U.S. Appl. No. 15/608,948, filed May 30, 2017.
U.S. Appl. No. 15/624,314 / U.S. Pat. No. 10,357,357, Jun. 15, 2017 / Jul. 23, 2019.
U.S. Appl. No. 15/650,783 / U.S. Pat. No. 10,639,459, Jul. 14, 2017 / May 5, 2020.
U.S. Appl. No. 15/656,936 / U.S. Pat. No. 10,478,594, Jul. 21, 2017 / Nov. 19, 2019.
U.S. Appl. No. 15/668,622 / U.S. Pat. No. 10,463,490, Aug. 3, 2017 / Nov. 5, 2019.
U.S. Appl. No. 15/798,250, filed Oct. 30, 2017.
U.S. Appl. No. 15/988,888, filed May 24, 2018.
U.S. Appl. No. 16/130,978 / U.S. Pat. No. 10,251,740, Sep. 13, 2018 / Apr. 9, 2019.
U.S. Appl. No. 16/130,988, filed Sep. 13, 2018.
U.S. Appl. No. 16/205,213, filed Nov. 29, 2018.
U.S. Appl. No. 16/374,698, filed Apr. 3, 2019.
U.S. Appl. No. 16/395,209, filed Apr. 25, 2019.
U.S. Appl. No. 16/408,419, filed May 9, 2019.
U.S. Appl. No. 16/505,624, filed Jul. 8, 2019.
U.S. Appl. No. 16/686,013, filed Nov. 15, 2019.

(56) References Cited

OTHER PUBLICATIONS

U.S. Appl. No. 16/866,377, filed May 4, 2020.
U.S. Appl. No. 16/875,652, filed May 15, 2020.
U.S. Appl. No. 15/650,783, filed Jul. 14, 2017.
U.S. Appl. No. 15/656,936, filed Jul. 21, 2017.
Boehm, et al., Balloon Atrial Septostomy: History and Technique, Images Paeditr. Cardiol., 8(1):8-14 (2006).
Drexel, et al., The Effects of Cold Work and Heat Treatment on the Properties of Nitinol Wire, Proceedings of the International Conference on Shape Memory and Superelastic Technologies, May 7-11, 2006, Pacific Grove, California, USA (pp. 447-454).
Eigler, et al., Implantation and Recovery of Temporary Metallic Stents in Canine Coronary Arteries, JACC, 22(4):1207-1213 (1993).
International Search Report & Written Opinion dated Feb. 7, 2020 in Int'l PCT Patent Appl. Serial No. PCT/IB2019/060257.
Partial International Search dated Aug. 17, 2017 in Int'l PCT Patent Appl. Serial No. PCT/IB2017/053188.
Partial Supplemental European Search Report dated Dec. 11, 2018 in EP Patent Appl. Serial No. 1678939.6.
Abraham et al., "Hemodynamic Monitoring in Advanced Heart Failure: Results from the LAPTOP-HF Trial," J Card Failure, 22:940 (2016) (Abstract Only).
Abraham et al., "Sustained efficacy of pulmonary artery pressure to guide adjustment of chronic heart failure therapy: complete follow-up results from the CHAMPION randomised trial," The Lancet, http://dx.doi.org/10.1016/S0140-6736(15)00723-0 (2015).
Abraham et al., "Wireless pulmonary artery haemodynamic monitoring in chronic heart failure: a randomised controlled trial," The Lancet, DOI:10.1016/S0140-6736(11)60101-3 (2011).
Abreu et al., "Doppler ultrasonography of the femoropopliteal segment in patients with venous ulcer," J Vasc Bras., 11(4):277-285 (2012).
Adamson et al., "Ongoing Right Ventricular Hemodynamics in Heart Failure Clinical Value of Measurements Derived From an Implantable Monitoring System," J Am Coll Cardiol., 41(4):565-571 (2003).
Adamson et al., "Wireless Pulmonary Artery Pressure Monitoring Guides Management to Reduce Decompensation in Heart Failure With Preserved Ejection Fraction," Circ Heart Fail., 7:935-944 (2014).
Ambrosy et al. "The Global Health and Economic Burden of Hospitalizations for Heart Failure," J Am Coll Cardiol., 63:1123-1133 (2014).
Aminde et al., "Current diagnostic and treatment strategies for Lutembacher syndrome: the pivotal role of echocardiography," Cardiovasc Diagn Ther., 5(2):122-132 (2015).
Anderas E. "Advanced MEMS Pressure Sensors Operating in Fluids," Digital Comprehensive Summaries of Uppsala Dissertation from the Faculty of Science and Technology 933. Uppsala ISBN 978-91-554-8369-2 (2012).
Anderas et al., "Tilted c-axis Thin-Film Bulk Wave Resonant Pressure Sensors with Improved Sensitivity," IEEE Sensors J., 12(8):2653-2654 (2012).
Article 34 Amendments dated May 28, 2013 in Int'l PCT Patent Appl. Serial No. PCT/IB2012/001859.
Article 34 Amendments dated Nov. 27, 2012 in Int'l PCT Patent Appl. Serial No. PCT/IL2011/000958.
Ataya et al., "A Review of Targeted Pulmonary Arterial Hypertension-Specific Pharmacotherapy," J. Clin. Med., 5(12):114(2016).
Bannan et al., "Characteristics of Adult Patients with Atrial Septal Defects Presenting with Paradoxical Embolism.," Catheterization and Cardiovascular Interventions, 74:1066-1069 (2009).
Baumgartner et al., "ESC Guidelines for the management of grown-up congenital heart disease (new version 2010)—The Task Force on the Management of Grown-up Congenital Heart Disease of the European Society of Cardiology (ESC)," Eur Heart J., 31:2915-2957 (2010).
Beemath et al., "Pulmonary Embolism as a Cause of Death in Adults Who Died With Heart Failure," Am J Cardiol., 98:1073-1075 (2006).

Benza et al., "Monitoring Pulmonary Arterial Hypertension Using an Implantable Hemodynamic Sensor," CHEST, 156(6):1176-1186 (2019).
Bruch et al., "Fenestrated Occluders for Treatment of ASD in Elderly Patients with Pulmonary Hypertension and/or Right Heart Failure," J Interven Cardiol., 21(1):44-49 (2008).
Burkhoff et al., "Assessment of systolic and diastolic ventricular properties via pressure-volume analysis: a guide for clinical, translational, and basic researchers," Am J Physiol Heart Circ Physiol., 289:H501-H512 (2005).
Butler et al. "Recognizing Worsening Chronic Heart Failure as an Entity and an End Point in Clinical Trials," JAMA., 312(8):789-790 (2014).
Chakko et al., "Clinical, radiographic, and hemodynamic correlations in chronic congestive heart failure: conflicting results may lead to inappropriate care," Am J Medicine, 90:353-359 (1991) (Abstract Only).
Chang et al., "State-of-the-art and recent developments in micro/nanoscale pressure sensors for smart wearable devices and health monitoring systems," Nanotechnology and Precision Engineering, 3:43-52 (2020).
Chen et al., "Continuous wireless pressure monitoring and mapping with ultra-small passive sensors for health monitoring and critical care," Nature Communications, 5(1):1-10 (2014).
Chen et al., "National and Regional Trends in Heart Failure Hospitalization and Mortality Rates for Medicare Beneficiaries, 1998-2008," JAMA, 306(15):1669-1678 (2011).
Chiche et al., "Prevalence of patent foramen ovale and stroke in pulmonary embolism patients," Eur Heart J., 34:P1142 (2013) (Abstract Only).
Chin et al., "The right ventricle in pulmonary hypertension," Coron Artery Dis., 16(1):13-18 (2005) (Abstract Only).
Chun et al., "Lifetime Analysis of Hospitalizations and Survival of Patients Newly Admitted With Heart Failure," Circ Heart Fail., 5:414-421 (2012).
Ciarka et al., "Atrial Septostomy Decreases Sympathetic Overactivity in Pulmonary Arterial Hypertension," Chest, 131(6):P1831-1837 (2007) (Abstract Only).
Cleland et al., "The EuroHeart Failure survey programme—a survey on the quality of care among patients with heart failure in Europe—Part 1: patient characteristics and diagnosis," Eur Heart J., 24:442-463 (2003).
Clowes et al., "Mechanisms of Arterial Graft Healing—Rapid Transmural Capillary Ingrowth Provides a Source of Intimal Endothelium and Smooth Muscle in Porous PTFE Prostheses," Am J Pathol., 123:220-230 (1986).
Davies et al., "Abnormal left heart function after operation for atrial septal defect," British Heart Journal, 32:747-753 (1970).
Del Trigo et al., "Unidirectional Left-To-Right Interatrial Shunting for Treatment of Patients with Heart Failure with Reduced Ejection Fraction: a Safety and Proof-of-Principle Cohort Study," Lancet, 387:1290-1297 (2016).
Della Lucia et al., "Design, fabrication and characterization of SAW pressure sensors for offshore oil and gas exploration," Sensors and Actuators A: Physical, 222:322-328 (2015).
Drazner et al., "Prognostic Importance of Elevated Jugular Venous Pressure and a Third Heart Sound in Patients with Heart Failure," N Engl J Med., 345(8):574-81 (2001).
Drazner et al., "Relationship between Right and Left-Sided Filling Pressures in 1000 Patients with Advanced Heart Failure," Heart Lung Transplant, 18:1126-1132 (1999).
Eigler et al., "Cardiac Unloading with an Implantable Interatrial Shunt in Heart Failure: Serial Observations in an Ovine Model of Ischemic Cardiomyopathy," Structural Heart, 1:40-48 (2017).
Eshaghian et al., "Relation of Loop Diuretic Dose to Mortality in Advanced Heart Failure," Am J Cardiol., 97:1759-1764 (2006).
Extended European Search Report dated Jan. 8, 2015 in EP Patent Appl No. 10772089.8.
Extended European Search Report dated Mar. 29, 2019 in EP Patent Appl. Serial No. EP16789391.
Feldman et al., "Transcatheter Interatrial Shunt Device for the Treatment of Heart Failure with Preserved Ejection Fraction (REDUCE

(56) References Cited

OTHER PUBLICATIONS

LAP-HF I [Reduce Elevated Left Atrial Pressure in Patients With Heart Failure]), A Phase 2, Randomized, Sham-Controlled Trial," Circulation, 137:364-375 (2018).
Ferrari et al., "Impact of pulmonary arterial hypertension (PAH) on the lives of patients and carers: results from an international survey," Eur Respir J., 42:26312 (2013) (Abstract Only).
Fonarow et al., "Characteristics, Treatments, and Outcomes of Patients With Preserved Systolic Function Hospitalized for Heart Failure," J Am Coll Cardiol., 50(8):768-777 (2007).
Fonarow et al., "Risk Stratification for In-Hospital Mortality in Acutely Decompensated Heart Failure: Classification and Regression Tree Analysis," JAMA, 293(5):572-580 (2005).
Fonarow, G., "The Treatment Targets in Acute Decompensated Heart Failure," Rev Cardiovasc Med., 2:(2):S7-S12 (2001).
Galie et al., "2015 ESC/ERS Guidelines for the diagnosis and treatment of pulmonary hypertension—The Joint Task Force for the Diagnosis and Treatment of Pulmonary Hypertension of the European Society of Cardiology (ESC) and the European Respiratory Society (ERS)," European Heart Journal, 37:67-119 (2016).
Galie et al., "Pulmonary arterial hypertension: from the kingdom of the near-dead to multiple clinical trial meta-analyses," Eur Heart J., 31:2080-2086 (2010).
Galipeau et al., "Surface acoustic wave microsensors and applications," Smart Materials and Structures, 6(6):658-667 (1997) (Abstract Only).
Geva et al., "Atrial septal defects," Lancet, 383:1921-32 (2014).
Gheorghiade et al., "Acute Heart Failure Syndromes, Current State and Framework for Future Research," Circulation, 112:3958-3968 (2005).
Gheorghiade et al., "Effects of Tolvaptan, a Vasopressin Antagonist, in Patients Hospitalized With Worsening Heart Failure A Randomized Controlled Trial," JAMA., 291:1963-1971 (2004).
Go et al. "Heart Disease and Stroke Statistics—2014 Update—A Report From the American Heart Association," Circulation, 128:1-267 (2014).
Guillevin et al., "Understanding the impact of pulmonary arterial hypertension on patients' and carers' lives," Eur Respir Rev., 22:535-542 (2013).
Guyton et al., "Effect of Elevated Left Atrial Pressure and Decreased Plasma Protein Concentration on the Development of Pulmonary Edema," Circulation Research, 7:643-657 (1959).
Hasenfub, et al., A Transcatheter Intracardiac Shunt Device for Heart Failure with Preserved Ejection Fraction (REDUCE LAP-HF): A Multicentre, Open-Label, Single-Arm, Phase 1 Trial, www.thelancet.com, 387:1298-1304 (2016).
Hoeper et al., "Definitions and Diagnosis of Pulmonary Hypertension," J Am Coll Cardiol., 62(5):D42-D50 (2013).
Hogg et al., "Heart Failure With Preserved Left Ventricular Systolic Function. Epidemiology, Clinical Characteristics, and Prognosis," J Am Coll Cardiol., 43(3):317-327 (2004).
Howell et al., "Congestive heart failure and outpatient risk of venous thromboembolism: A retrospective, case-control study," Journal of Clinical Epidemiology, 54:810-816 (2001).
Huang et al., "Remodeling of the chronic severely failing ischemic sheep heart after coronary microembolization: functional, energetic, structural, and cellular responses," Am J Physiol Heart Circ Physiol., 286:H2141-H2150 (2004).
Humbert et al., "Pulmonary Arterial Hypertension in France—Results from a National Registry," Am J Respir Crit Care Med., 173:1023-1030 (2006).
International Search Report & Written Opinion dated Nov. 7, 2016 in Int'l PCT Patent Appl. Serial No. PCT/IB2016/052561.
International Search Report & Written Opinion dated May 29, 2018 in Int'l PCT Patent Appl. Serial No. PCT/IB2018/051385.
International Search Report & Written Opinion dated Feb. 6, 2013 in Int'l PCT Patent Appl. No. PCT/IB2012/001859, 12 pages.
International Search Report & Written Opinion dated May 13, 2019 in Int'l PCT Patent Appl. No. PCT/IB2019/050452.

International Search Report & Written Opinion dated Jul. 14, 2020 in Int'l PCT Patent Appl. Serial No. PCT/IB2020/053832.
International Search Report & Written Opinion dated Jul. 20, 2020 in Int'l PCT Patent Appl. Serial No. PCT/IB2020/054699.
International Search Report & Written Opinion dated Aug. 12, 2020 in Int'l PCT Patent Appl. Serial No. PCT/IB2020/053118.
International Search Report & Written Opinion dated Aug. 28, 2012 in Int'l PCT Patent Appl. No. PCT/IL2011/000958.
International Search Report & Written Opinion dated Sep. 21, 2020 in Int'l PCT Patent Appl. Serial No. PCT/IB2020/054306.
International Search Report & Written Opinion dated Oct. 26, 2007 in Int'l PCT Patent Appl. Serial No. PCT/IB07/50234.
International Search Report dated Sep. 20, 2016 in Int'l PCT Patent Appl. Serial No. PCT/IB2016/052561.
Jessup et al. "2009Focused Update: ACC/AHA Guidelines for the Diagnosis and Management of Heart Failure in Adults: A Report of the American College of Cardiology Foundation/American Heart Association Task Force on Practice Guidelines: Developed in Collaboration With the International Society for Heart and Lung Transplantation," J. Am. Coll. Cardiol., 53:1343-1382 (2009).
Jiang, G., "Design challenges of implantable pressure monitoring system," Frontiers in Neuroscience, 4(29):1-4 (2010).
Kane et al., "Integration of clinical and hemodynamic parameters in the prediction of long-term survival in patients with pulmonary arterial hypertension," Chest, 139(6):1285-1293 (2011) (Abstract Only).
Kaye et al., "Effects of an Interatrial Shunt on Rest and Exercise Hemodynamics: Results of a Computer Simulation in Heart Failure," Journal of Cardiac Failure, 20(3): 212-221 (2014).
Kaye et al., "One-Year Outcomes After Transcatheter Insertion of an Interatrial Shunt Device for the Management of Heart Failure With Preserved Ejection Fraction," Circulation: Heart Failure, 9(12):e003662 (2016).
Keogh et al., "Interventional and Surgical Modalities of Treatment in Pulmonary Hypertension," J Am Coll Cardiol., 54:S67-77 (2009).
Keren, et al. Methods and Apparatus for Reducing Localized Circulatory System Pressure,., Jan. 7, 2002 (pp. 16).
Kretschmar et al., "Shunt Reduction With a Fenestrated Amplatzer Device," Catheterization and Cardiovascular Interventions, 76:564-571 (2010).
Kropelnicki et al., "CMOS-compatible ruggedized high-temperature Lamb wave pressure sensor," J. Micromech. Microeng., 23:085018 pp. 1-9 (2013).
Krumholz et al., "Patterns of Hospital Performance in Acute Myocardial Infarction and Heart Failure 30-Day Mortality and Readmission," Circ Cardiovasc Qual Outcomes, 2:407-413 (2009).
Kulkarni et al., "Lutembacher's syndrome," J Cardiovasc Did Res., 3(2):179-181 (2012).
Kurzyna et al., "Atrial Septostomy in Treatment of End-Stage Right Heart Failure in Patients With Pulmonary Hypertension," Chest, 131:977-983 (2007).
Lammers et al., "Efficacy and Long-Term Patency of Fenerstrated Amplatzer Devices in Children," Catheter Cardiovasc Interv., 70:578-584 (2007).
Lindenfeld et al. "Executive Summary: HFSA 2010 Comprehensive Heart Failure Practice Guideline," J. Cardiac Failure, 16(6):475-539 (2010).
Luo, Yi, *Selective and Regulated RF Heating of Stent Toward Endohyperthermia Treatment of In-Stent Restenosis*, A Thesis Submitted in Partial Fulfillment of The Requirements For The Degree of Master of Applied Science in The Faculty of Graduate and Postdoctoral Studies (Electrical and Computer Engineering), The University of British Columbia, Vancouver, Dec. 2014.
MacDonald et al., "Emboli Enter Penetrating Arteries of Monkey Brain in Relation to Their Size," Stroke, 26:1247-1251 (1995).
Maluli et al., "Atrial Septostomy: A Contemporary Review," Clin. Cardiol., 38(6):395-400 (2015).
Maurer et al., "Rationale and Design of the Left Atrial Pressure Monitoring to Optimize Heart Failure Therapy Study (LAPTOP-HF)," Journal of Cardiac Failure., 21(6): 479-488 (2015).

(56) References Cited

OTHER PUBLICATIONS

McClean et al., "Noninvasive Calibration of Cardiac Pressure Transducers in Patients With Heart Failure: An Aid to Implantable Hemodynamic Monitoring and Therapeutic Guidance," J Cardiac Failure, 12(7):568-576 (2006).
McLaughlin et al., "Management of Pulmonary Arterial Hypertension," J Am Coll Cardiol., 65(18):1976-1997 (2015).
McLaughlin et al., "Survival in Primary Pulmonary Hypertension—The Impact of Epoprostenol Therapy.," Circulation, 106:1477-1482 (2002).
Mu et al., "Dual mode acoustic wave sensor for precise pressure reading," Applied Physics Letters, 105:113507-1-113507-5 (2014).
Nagaragu et al., "A 400µW Differential FBAR Sensor Interface IC with digital readout," IEEE., pp. 218-221 (2015).
Noordegraaf et al., "The role of the right ventricle in pulmonary arterial hypertension," Eur Respir Rev., 20(122):243-253 (2011).
O'Byrne et al., "The effect of atrial septostomy on the concentration of brain-type natriuretic peptide in patients with idiopathic pulmonary arterial hypertension," Cardiology in the Young, 17(5):557-559 (2007) (Abstract Only).
Oktay et al., "The Emerging Epidemic of Heart Failure with Preserved Ejection Fraction," Curr Heart Fail Rep., 10(4):1-17 (2013).
Owan et al., "Trends in Prevalence and Outcome of Heart Failure with Preserved Ejection Fraction," N Engl J Med., 355:251-259 (2006).
Paitazoglou et al., "Title: The AFR-PRELIEVE Trial: A prospective, non-randomized, pilot study to assess the Atrial Flow Regulator (AFR) in Heart Failure Patients with either preserved or reduced ejection fraction," EuroIntervention, 28:2539-50 (2019).
Peters et al., "Self-fabricated fenestrated Amplatzer occluders for transcatheter closure of atrial septal defect in patients with left ventricular restriction: midterm results," Clin Res Cardiol., 95:88-92 (2006).
Ponikowski et al., "2016 ESC Guidelines for the diagnosis and treatment of acute and chronic heart failure. The Task Force for the diagnosis and treatment of acute and chronic heart failure of the European Society of Cardiology (ESC)," Eur Heart J., doi:10.1093/eurheartj/ehw128 (2016).
Potkay, J. A., "Long term, implantable blood pressure monitoring systems," Biomed Microdevices, 10:379-392 (2008).
Pretorious et al., "An Implantable Left Atrial Pressure Sensor Lead Designed for Percutaneous Extraction Using Standard Techniques," PACE, 00:1-8 (2013).
Rajeshkumar et al., "Atrial septostomy with a predefined diameter using a novel occlutech atrial flow regulator improves symptoms and cardiac index in patients with severe pulmonary arterial hypertension," Catheter Cardiovasc Interv., 1-9 (2017).
Rich et al., "Atrial Septostomy as Palliative Therapy for Refractory Primary Pulmonary Hypertension," Am J Cardiol. 51:1560-1561 (1983).
Ritzema et al., "Direct Left Atrial Pressure Monitoring in Ambulatory Heart Failure Patients—Initial Experience With a New Permanent Implantable Device," Circulation, 116:2952-2959 (2007).
Ritzema et al., "Physician-Directed Patient Self-Management of Left Atrial Pressure in Advanced Chronic Heart Failure," Circulation, 121:1086-1095 (2010).
Roberts et al., "Integrated microscopy techniques for comprehensive pathology evaluation of an implantable left atrial pressure sensor," J Histotechnology, 36(1):17-24 (2013).
Rodes-Cabau et al., "Interatrial Shunting for Heart Failure Early and Late Results From the First-in-Human Experience With the V-Wave System," J Am Coll Cardiol Intv., 11:2300-2310.doi:10.1016/j.cin.2018.07.001 (2018).
Rosenquist et al., Atrial Septal Thickness and Area in Normal Heart Specimens and in Those With Ostium Secundum Atrial Septal Defects, J. Clin. Ultrasound, 7:345-348 (1979).
Ross et al., "Interatrial Communication and Left Atrial Hypertension—A Cause of Continuous Murmur," Circulation, 28:853-860 (1963).
Rossignol, et al., Left-to-Right Atrial Shunting: New Hope for Heart Failure, www.thelancet.com, 387:1253-1255 (2016).
Sandoval et al., "Effect of atrial septostomy on the survival of patients with severe pulmonary arterial hypertension," Eur Respir J., 38:1343-1348 (2011).
Sandoval et al., "Graded Balloon Dilation Atrial Septostomy in Severe Primary Pulmonary Hypertension—A Therapeutic Alternative for Patients Nonresponsive to Vasodilator Treatment," JACC, 32(2):297-304 (1998).
Schiff et al., "Decompensated heart failure: symptoms, patterns of onset, and contributing factors," Am J. Med., 114(8):625-630 (2003) (Abstract Only).
Schneider et al., "Fate of a Modified Fenestration of Atrial Septal Occluder Device after Transcatheter Closure of Atrial Septal Defects in Elderly Patients," J Interven Cardiol., 24:485-490 (2011).
Scholl et al., "Surface Acoustic Wave Devices for Sensor Applications," Phys Status Solidi Appl Res., 185(1):47-58 (2001) (Abstract Only).
Setoguchi et al., "Repeated hospitalizations predict mortality in the community population with heart failure," Am Heart J., 154:260-266 (2007).
Shah et al., "Heart Failure With Preserved, Borderline, and Reduced Ejection Fraction—5-Year Outcomes," J Am Coll Cardiol., https://doi.org/10.1016/j.jacc.2017.08.074 (2017).
Shah et al., "One-Year Safety and Clinical Outcomes of a Transcatheter Interatrial Shunt Device for the Treatment of Heart Failure With Preserved Ejection Fraction in the Reduce Elevated Left Atrial Pressure in Patients With Heart Failure (REDUCE LAP-HFI) Trial—A Randomized Clinical Trial," JAMA Cardiol. doi:10.1001/jamacardio.2018.2936 (2018).
Sitbon et al., "Selexipag for the Treatment of Pulmonary Arterial Hypertension.," N Engl J Med., 373(26):2522-2533 (2015).
Sitbon et al., "Epoprostenol and pulmonary arterial hypertension: 20 years of clinical experience," Eur Respir Rev., 26:160055:1-14 (2017).
Steimle et al., "Sustained Hemodynamic Efficacy of Therapy Tailored to Reduce Filling Pressures in Survivors With Advanced Heart Failure," Circulation, 96:1165-1172 (1997).
Stevenson et al., "The Limited Reliability of Physical Signs for Estimating Hemodynamics in Chronic Heart Failure," JAMA, 261(6):884-888 (1989) (Abstract Only).
Su et al., "A film bulk acoustic resonator pressure sensor based on lateral field excitation," International Journal of DistributedSensor Networks, 14(11):1-8 (2018).
Supplementary European Search Report dated Nov. 13, 2009 in EP Patent Appl. Serial No. 05703174.2.
Thenappan et al., "Evolving Epidemiology of Pulmonary Arterial Hypertension," Am J Resp Critical Care Med., 186:707-709 (2012).
Tomai et al., "Acute Left Ventricular Failure After Transcatheter Closure of a Secundum Atrial Septal Defect in a Patient With Coronary Artery Disease: A Critical Reappraisal," Catheterization and Cardiovascular Interventions, 55:97-99 (2002).
Torbicki et al., "Atrial Septostomy," The Right Heart, 305-316 (2014).
Troost et al., "A Modified Technique of Stent Fenestration of the Interatrial Septum Improves Patients With Pulmonary Hypertension," Catheterization and Cardiovascular Interventions, 73:173179 (2009).
Troughton et al., "Direct Left Atrial Pressure Monitoring in Severe Heart Failure: Long-Term Sensor Performance," J. of Cardiovasc. Trans. Res., 4:3-13 (2011).
Vank-Noordegraaf et al., "Right Heart Adaptation to Pulmonary Arterial Hypertension—Physiology and Pathobiology," J Am Coll Cardiol., 62(25):D22-33 (2013).
Verel et al., "Comparison of left atrial pressure and wedge pulmonary capillary pressure—Pressure gradients between left atrium and left ventricle," British Heart J., 32:99-102 (1970).
Viaene et al., "Pulmonary oedema after percutaneous ASD-closure," Acta Cardiol., 65(2):257-260 (2010).
Wang et al., "A Low Temperature Drifting Acoustic Wave Pressure Sensor with an Integrated Vacuum Cavity for Absolute Pressure Sensing," Sensors, 20(1788):1-13 (2020).

(56) References Cited

OTHER PUBLICATIONS

Wang et al., "Tire Pressure Monitoring System and Wireless Passive Surface Acoustic Wave Sensor," Appl Meeh Mater., 536(537):333-337 (2014).
Warnes et al., "ACC/AHA 2008 Guidelines for the Management of Adults With Congenital Heart Disease—A Report of the American College of Cardiology/American Heart Association Task Force on Practice Guidelines (Writing Committee to Develop Guidelines on the Management of Adults With Congenital Heart Disease)," JACC, 52(23):e143-e263 (2008).
Webb et al., "Atrial Septal Defects in the Adult Recent Progress and Overview," Circulation, 114:1645-1653 (2006).
Wiedemann, H.R., "Earliest description by Johann Friedrich Meckel, Senior (1750) of what is known today as Lutembacher syndrome (1916)," Am J Med Genet., 53(1):59-64 (1994) (Abstract Only).
Written Opinion of the International Searching Authority dated Apr. 7, 2008 in Int'l PCT Patent Appl. Serial No. PCT/IL05/00131.
Yantchev et al., "Thin Film Lamb Wave Resonators in Frequency Control and Sensing Applications: A Review," Journal of Micromechanics and Microengineering, 23(4):043001 (2013).
Zhang et al., "Acute left ventricular failure after transcatheter closure of a secundum atrial septal defect in a patient with hypertrophic cardiomyopathy," Chin Med J., 124(4):618-621 (2011).
Zhang et al., "Film bulk acoustic resonator-based high-performance pressure sensor integrated with temperature control system," J Micromech Microeng., 27(4):1-10 (2017).
Ando et al., "Left ventricular decompression through a patent foramen ovale in a patient with hypertropic cardiomyopathy: A case report," Cardiovascular Ultrasound 2: 1-7 (2004).
Braunwald, Heart Disease, Chapter 6, p. 186.
Bridges, et al., The Society of Thoracic Surgeons Practice Guideline Series: Transmyocardial Laser Revascularization, Ann Thorac Surg., 77:1494-1502 (2004).
Bristow et al., "Improvement in cardiac myocite function by biological effects of medical therapy: a new concept in the treatment of heart failure," European Heart Journal 16(Suppl. F): 20-31 (1995).
Case et al., "Relief of High Left-Atrial Pressure in Left-Ventricular Failure," Lancet, pp. 841-842 (Oct. 14, 1964).
Coats et al., "Controlled trial of physical training in chronic heart failure: Exercise performance, hemodynamics, ventilation and autonomic function," Circulation 85:2119-2131 (1992).
Davies et al., "Reduced contraction and altered frequency response of isolated ventricular myocytes from patients with heart failure," Circulation 92: 2540-2549 (1995).
Ennezat et al., "An unusual case of low-flow, low-gradient severe aortic stenosis: Left-to-right shunt due to atrial septal defect," Cardiology 113(2): 146-148 (2009).
Ewert et al., "Acute left heart failure after interventional occlusion of an atrial septal defect," Z Kardiol. 90(5): 362-366 (May 2001).
Ewert, et al., Masked Left Ventricular Restriction in Elderly Patients with Atrial Septal Defects: A Contraindication for Closure, Catherization and Cardiovascular Interventions, 52:177-180 (2001).
Extended EP Search Report dated Sep. 19, 2016 in EP Patent Application Serial No. 16170281.6.
Final Office Action dated Jan. 5, 2009 in U.S. Appl. No. 10/597,666.
Geiran et al., "Changes in cardiac dynamics by opening an interventricular shunt in dogs," J. Surg. Res. 48(1): 6-12 (Jan. 1990).
Gelernter-Yaniv et al., "Transcatheter closure of left-to-right interatrial shunts to resolve hypoxemia," Conginit. Heart Dis. 31(1) 47-53 (Jan. 2008).
Gewillig et al., "Creation with a stent of an unrestrictive lasting atrial communication," Cardio. Young 12(4): 404-407 (2002).
International Preliminary Report on Patentability & Written Opinion dated Aug. 7, 2008 in Int'l PCT Patent Application Serial No. PCT/IB2007/050234.
International Search Report for PCT/IL2005/000131, 3 pages (dated Apr. 7, 2008).
International Search Report for PCT/IL2010/000354 dated Aug. 25, 2016 (1 pg).
ISR & Written Opinion dated Feb. 16, 2015 in Int'l PCT Patent Appl. Serial No. PCT/IB2014/001771.
Khositseth et al., Transcatheter Amplatzer Device Closure of Atrial Septal Defect and Patent Foramen Ovale in Patients With Presumed Paradoxical Embolism, Mayo Clinic Proc., 79:35-41 (2004).
Kramer et al., "Controlled study of captopril in chronic heart failure: A rest and exercise hemodynamic study," Circulation 67(4): 807-816 (1983).
Lai et al., "Bidirectional shunt through a residual atrial septal defect after percutaneous transvenous mitral commissurotomy," Cardiology 83(3): 205-207 (1993).
Lemmer et al., "Surgical implications of atrial septal defect complicating aortic balloon valvuloplasty," Ann Thorac. Surg. 48(2): 295-297 (Aug. 1989).
Merriam-Webster "Definition of 'Chamber'," Online Dictionary 2004, Abstract.
Park Blade Septostomy Catheter Instructions for Use, Cook Medical, 28 pages, Oct. 2015.
Park, et al., Blade Atrial Septostomy: Collaborative Study, Circulation, 66(2):258-266 (1982).
Preliminary Amendment dated Aug. 3, 2006 in U.S. Appl. No. 10/597,666.
Preliminary Amendment dated Jan. 13, 2014 in U.S. Appl. No. 14/154,093.
Preliminary Amendment dated Oct. 6, 2011 in U.S. Appl. No. 13/108,850.
Preliminary Amendment dated Oct. 6, 2011 in U.S. Appl. No. 13/108,672.
Response Non-Final Office Action dated Sep. 17, 2009 in U.S. Appl. No. 10/597,666.
Response Non-Final Office Action dated Oct. 7, 2013 in U.S. Appl. No. 13/108,672.
Response After Final Office Action dated Mar. 2, 2009 in U.S. Appl. No. 10/597,666.
Response After Final Office Action dated Mar. 8, 2010 in U.S. Appl. No. 10/597,666.
Response Final Office Action dated Jan. 23, 2014 in U.S. Appl. No. 13/108,698.
Response Final Office Action dated Mar. 14, 2017 in U.S. Appl. No. 14/154,093.
Response Final Office Action dated Apr. 20, 2016 in U.S. Appl. No. 13/108,698.
Response Final Office Action dated Apr. 20, 2016 in U.S. Appl. No. 13/108,850.
Response Final Office Action dated Apr. 30, 2014 in U.S. Appl. No. 13/108,672.
Response Final Office Action dated Oct. 28, 2014 in U.S. Appl. No. 13/108,698.
Response Final Office Action dated Nov. 11, 2013 in U.S. Appl. No. 13/108,698.
Response Final Office Action dated Nov. 21, 2013 in U.S. Appl. No. 13/108,698.
Response Final Office Action dated Feb. 11, 2016 in U.S. Appl. No. 14/154,093.
Response Non-Compliant Amendment dated Sep. 23, 2016 in U.S. Appl. No. 13/108,672.
Response Non-Final Office Action dated Jan. 6, 2017 in U.S. Appl. No. 13/108,698.
Response Non-Final Office Action dated Jan. 6, 2017 in U.S. Appl. No. 13/108,850.
Response NonFinal Office Action dated May 1, 2014 in related U.S. Appl. No. 13/108,850.
Response NonFinal Office Action dated May 1, 2014 in U.S. Appl. No. 13/108,698.
Response Non-Final Office Action dated May 20, 2016 in U.S. Appl. No. 13/108,672.
Response NonFinal Office Action dated Jun. 13, 2012 in U.S. Appl. No. 13/308,698.
Response Non-Final Office Action dated Jul. 9, 2015 in U.S. Appl. No. 13/108,698.
Response Non-Final Office Action dated Jul. 9, 2015 in U.S. Appl. No. 13/108,850.

(56) References Cited

OTHER PUBLICATIONS

Response NonFinal Office Action dated Aug. 28, 2008 in related U.S. Appl. No. 10/597,666.
Response NonFinal Office Action dated Oct. 7, 2013 in related U.S. Appl. No. 13/108,850.
Response Non-Final Office Action dated Apr. 20, 2015 in U.S. Appl. No. 14/154,093.
Response Non-Final Office Action dated Jun. 10, 2016 in U.S. Appl. No. 14/154,093.
Response Restriction Requirement dated Sep. 27, 2012 in U.S. Appl. No. 13/108,698.
Response Restriction Requirement dated May 20, 2013 in U.S. Appl. No. 13/108,850.
Response to Final Office Action dated Oct. 28, 2014 in U.S. Appl. No. 13/108,850.
Response to Restriction Requirement dated Jul. 2, 2012 in U.S. Appl. No. 13/108,672.
Restriction Requirement dated Feb. 20, 2013 in U.S. Appl. No. 13/108,850.
Restriction Requirement dated Jun. 7, 2012 in U.S. Appl. No. 13/108,672.
Roven et al., "Effect of Compromising Right Ventricular Function in Left Ventricular Failure by Means of Interatrial and Other Shunts," American Journal Cardiology, 24:209-219 (1969).
Salehian et al., Improvements in Cardiac Form and Function After Transcatheter Closure of Secundum Atrial Septal Defects, Journal of the American College of Cardiology, 45(4):499-504 (2005).
Schmitto et al., Chronic heart failure induced by multiple sequential coronary microembolization in sheep, The International Journal of Artificial Organs, 31(4):348-353 (2008).
Schubert et al., "Left ventricular conditioning in the elderly patient to prevent congestive heart failure after transcatheter closure of the atrial septal defect," Catheterization and Cardiovascular Interventions, 64(3): 333-337 (2005).
Stormer et al., "Comparative study of in vitro flow characteristics between a human aortic valve and a designed aortic valve and six corresponding types of prosthetic heart valves," European Surgical Research 8(2): 117-131 (1976).
Stumper et al., "Modified technique of stent fenestration of the atrial septum," Heart 89: 1227-1230 (2003).
Trainor et al., Comparative Pathology of an Implantable Left Atrial Pressure Sensor, ASAIO Journal, Clinical Cardiovascular/Cardiopulmonary Bypass, 59(5):486-92 (2013).
U.S. Final Office Action dated Jan. 7, 2010 in U.S. Appl. No. 10/597,666.
U.S. Notice of Allowance dated Oct. 6, 2011 in U.S. Appl. No. 10/597,666.
U.S. Office Action dated Mar. 13, 2012 in U.S. Appl. No. 13/108,698.
U.S. Office Action dated Mar. 24, 2009 in U.S. Appl. No. 10/597,666.
U.S. Office Action dated Mar. 28, 2008 in U.S. Appl. No. 10/597,666.
U.S. Restriction Requirement dated Aug. 28, 2012 in U.S. Appl. No. 13/108,698.
U.S. Final Office Action dated Jan. 31, 2014 in U.S. Appl. No. 13/108,672.
U.S. Final Office Action dated Sep. 26, 2016 in U.S. Appl. No. 14/154,093.
U.S. Final Office Action dated Apr. 19, 2017 in U.S. Appl. No. 13/108,850.
U.S. Final Office Action dated May 4, 2017 in U.S. Appl. No. 13/108,698.
U.S. Non-Final Office Action dated Jan. 21, 2016 in U.S. Appl. No. 13/108,672.
U.S. Non-Final Office Action dated Apr. 12, 2017 in U.S. Appl. No. 14/154,093.
U.S. Non-Final Office Action dated Jun. 27, 2013 in U.S. Appl. No. 13/108,850.
U.S. Non-Final Office Action dated Mar. 10, 2016 in U.S. Appl. No. 14/154,093.
U.S. Non-Final Office Action dated Jul. 8, 2016 in U.S. Appl. No. 13/108,698.
U.S. Non-Final Office Action dated Jul. 8, 2016 in U.S. Appl. No. 13/108,850.
U.S. Notice of Allowance dated May 5, 2017 in U.S. Appl. No. 13/108,672.
U.S. Office Action dated Jan. 15, 2015 in U.S. Appl. No. 13/108,698.
U.S. Office Action dated Jan. 16, 2014 in U.S. Appl. No. 13/108,850.
U.S. Office Action dated Mar. 26, 2014 in U.S. Appl. No. 13/108,698.
U.S. Office Action dated May 21, 2014 in U.S. Appl. No. 13/108,850.
U.S. Office Action dated May 21, 2014 in U.S. Appl. No. 13/108,698.
U.S. Office Action dated Sep. 11, 2013 in U.S. Appl. No. 13/108,698.
U.S. Office Action dated Jan. 14, 2015 in U.S. Appl. No. 13/108,850.
U.S. Office Action dated Oct. 21, 2014 in U.S. Appl. No. 14/154,093.
U.S. Office Action dated Oct. 21, 2015 in Appl. U.S. Appl. No. 13/108,850.
U.S. Office Action dated Oct. 22, 2015 in U.S. Appl. No. 13/108,698.
U.S. Office Action dated May 22, 2013 in U.S. Appl. No. 13/108,672.
U.S. Office Action dated Aug. 14, 2015 in U.S. Appl. No. 14/154,093.
U.S. Supplemental Notice of Allowability dated Jun. 29, 2017 in U.S. Appl. No. 13/108,672.
Zhou et al., Unidirectional Valve Patch for Repair of Cardiac Septal Defects With Pulmonary Hypertension, Annals of Thoracic Surgeons, 60:1245-1249 (1995).
Communication Relating to Results of the Partial International Search & Invitation to Pay Additional Search Fees dated Aug. 17, 2017 in Int'l PCT Patent Appl. Serial No. PCT/IB2017/053188.
"Atrium Advanta V12, Balloon Expandable Covered Stent, Improving Patient Outcomes with An Endovascular Approach," Brochure, 8 pages, Getinge (2017).
International Search Report & Written Opinion dated May 29, 2018 in Int'l PCT Patent Appl. Serial No. PCTIB2018/051355.
International Search Report & Written Opinion dated Jul. 23, 2021 in Int'l PCT Patent Appl. Serial No. PCT/IB2021/053594.
Non-Final Office Action dated Oct. 16, 2020 in U.S. Appl. No. 16/878,228.
Non-Final Office Action dated Nov. 21, 2018 in U.S. Appl. No. 15/668,622.
Notice of Allowance dated Jun. 17, 2019 in U.S. Appl. No. 15/668,622.
Notice of Allowance dated Dec. 10, 2020 in U.S. Appl. No. 16/878,228.
Response to Non-Final Office Action dated Feb. 19, 2019 in U.S. Appl. No. 15/668,622.
Response to Non-Final Office Action dated Oct. 23, 2020 in U.S. Appl. No. 16/878,228.
Response to Restriction Requirement dated Jul. 10, 2020 in U.S. Appl. No. 16/878,228.
Restriction Requirement dated Jul. 9, 2020 in U.S. Appl. No. 16/878,228.
Second Preliminary Amendment dated May 8, 2018 in U.S. Appl. No. 15/668,622.

\* cited by examiner

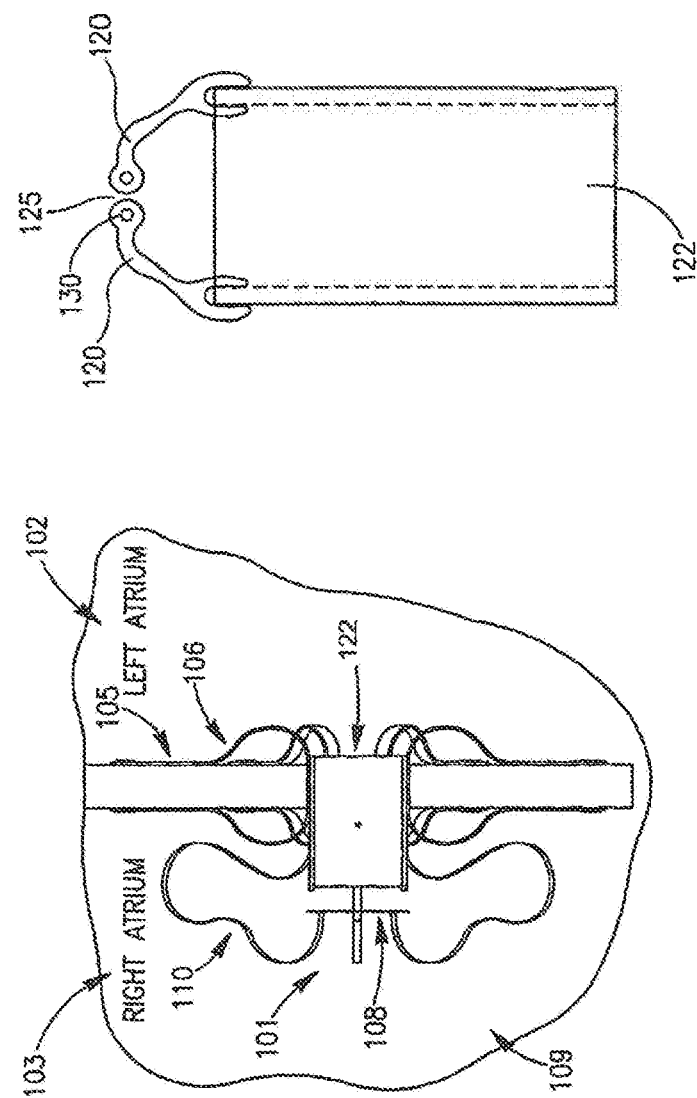

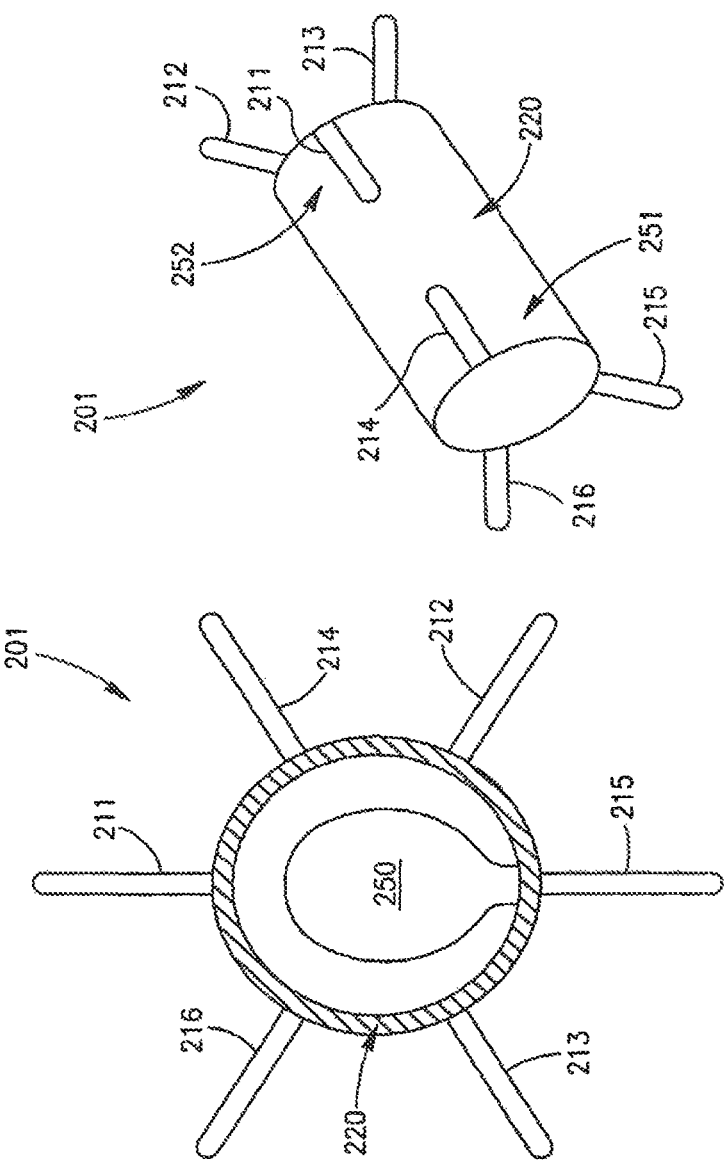

DEVICE AND METHOD FOR CONTROLLING IN-VIVO PRESSURE

CROSS-REFERENCE TO RELATED APPLICATIONS

This application is a continuation of U.S. patent application Ser. No. 15/668,622, filed Aug. 3, 2017, now U.S. Pat. No. 10,463,490, which is a divisional application of U.S. patent application Ser. No. 13/108,672, filed May 16, 2011, now U.S. Pat. No. 9,724,499, which is a continuation under 35 U.S.C. § 120 of U.S. patent application Ser. No. 10/597,666, filed Jun. 20, 2007, now U.S. Pat. No. 8,070,708, and entitled "Device and Method for Controlling In-Vivo Pressure," which is a U.S. national stage filing under 35 U.S.C. § 371 of International Patent Application No. PCT/IL2005/000131, filed Feb. 3, 2005, which claims the benefit of U.S. Provisional Patent Application No. 60/541,267, filed Feb. 3, 2004, and U.S. Provisional Patent Application No. 60/573,378, filed May 24, 2004, the entire contents of each of which are incorporated by reference herein.

FIELD OF THE INVENTION

The present invention relates to devices and methods for reducing or regulating pressure within a circulatory system, and in particular to regulate blood pressure in a heart.

BACKGROUND OF THE INVENTION

CHF is recognized as one of the most common causes of hospitalization and mortality in Western society, and has a great impact on the quality of life. CHF is a disorder characterized by low systemic perfusion and inefficient cardiac function. CHF causes may include myocardial Insult due to ischemia, cardiomyopathy and other processes. Pathophysiologic mechanisms that are directly associated with CHF include reduced cardiac output, increase in cardiac filling pressures, and fluid accumulation, which may lead to, for example, pulmonar congestion and dyspnea. Impairment of systolic function may result in poor left ventricular contraction and reduced cardiac output, which may generate clinical symptoms including effort intolerance, dyspnea, reduced longevity, edema (lung or peripheral) and pain. A patient with systolic dysfunction may usually have a larger left ventricle because of phenomena called cardiac remodeling aimed to maintain adequate stroke-volume. This pathophislologic mechanism is associated with increased atrial pressure and left ventricular filling pressure. With abnormal diastolic function, the left ventricle may be stiff and markedly less compliant partly because of abnormal relaxation leading to inadequate cardiac filling at normal pressures. Maintenance of adequate cardiac filling at higher filling pressures may be needed to maintain cardiac output. This mandatory rise of filling pressure to maintain cardiac filling and output may lead to pulmonary venous hypertension and lung edema.

Presently available treatments for CHF fall into three generally categories: (1) pharmacological, e.g., diuretics; (2) assist systems, e.g., pumps; and (3) surgical treatments. With respect to pharmacological treatments, vasodilators have been used to reduce the workload of the heart by reducing systemic vascular resistance and diuretics to prevent fluid accumulation and edema formation, and reduce cardiac filling pressure.

Assist devices used to treat CHF may include, for example, mechanical pumps. Mechanical pumps reduce the load on the heart by performing all or part of the pumping function normally done by the heart. Currently, mechanical pumps are used, for example, to sustain the patient while a donor heart for transplantation becomes available for the patient. There are also a number of pacing devices used to treat CHF. Resysnchronizatlon pacemakers have also been used to treat CHF. Finally, there are at least three extremely invasive and complex surgical procedures for treatment of heart failure: 1) heart transplant; 2) dynamic cardiomyoplasty; and 3) the Batista partial left ventriculectomy.

In extreme acute situations, temporary assist devices and intraaortic balloons may be helpful. Cardiac transplantation and chronic left ventricular assist device (LVAD) implants may often be used as last resort. However, all the assist devices currently used are intended to improve pumping capacity of the heart and increase cardiac output to levels compatible with normal life, reducing filling pressures and/or preventing edema formation. Finally, cardiac transplantation may be used to treat extreme cardiac dysfunction cases, however this procedure is highly invasive and is limited by the availability of donor hearts. The mechanical devices may allow propulsion of significant amount of blood (liters/min) and this is also their main limitation. The need for power supply, relatively large pumps and possibility of hemolysis and infection are all of concern.

BRIEF DESCRIPTION OF THE DRAWINGS

The subject matter regarded as the invention is particularly pointed out and distinctly claimed in the concluding portion of the specification. The invention, however, both as to organization and method of operation, together with features and advantages thereof, may best be understood by reference to the following detailed description when read with the accompanied drawings in which:

FIG. 1A is a schematic illustration of a Differential Pressure Regulation Device (DPRD), in accordance with an exemplary embodiment of the invention;

FIGS. 1B-1I are schematic illustrations of additional embodiments of Differential Pressure Regulation Devices (DPRD), in accordance with some embodiments of the invention;

FIGS. 2A and 2B are schematic illustrations of a cross-section view and a side view, respectively, of an adjustable shunt, tube or other structure in accordance with an exemplary embodiment of the invention;

Figure 1C:
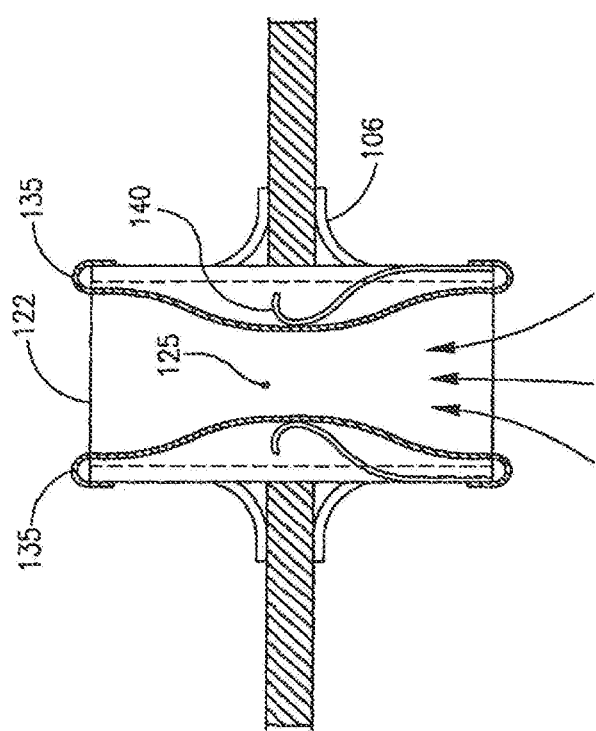

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

SUMMARY

The present invention may provide methods and devices for regulating pressure in a body. According to some embodiments of the present invention, a differential pressure regulating device may include a shunt being positioned between two or more lumens in a body, to enable fluids to flow between the lumens, and an adjustable flow regulation mechanism being configured to selectively cover an opening of the shunt, to regulate the flow of fluid through the shunt in relation to a pressure difference between the body lumens.

According to some embodiments the pressure regulating device may include a shunt being positioned between two or more chambers in a heart, to enable fluids to flow between the chambers, an adjustable flow regulation mechanism being configured to selectively cover the opening of the shunt, to regulate the flow of fluid through the shunt, and a control mechanism to be coupled to the adjustable flow regulation mechanism, to remotely activate the adjustable flow regulation mechanism.

In another embodiment a method is provided to control in-vivo pressure, which may include implanting a differential pressure regulation device in a body, the pressure regulation device including a shunt placed between two or more lumens in a body, deploying a flow regulation mechanism, and controlling the flow regulation mechanism setting according to changes in pressure differences between the lumens.

In a further embodiment of the present invention a method is provided to control in-vivo pressure, which may include controlling a flow regulation mechanism flow setting using a control mechanism implanted in a body, the flow regulation mechanism being disposed within a differential pressure regulation device that includes a shunt placed between two or more lumens, for example, between a left atrium of a heart and a right atrium of a heart.

DETAILED DESCRIPTION OF EMBODIMENTS OF THE PRESENT INVENTION

In the following detailed description, numerous specific details are set forth in order to provide a thorough understanding of the invention. However, it will be understood by those of ordinary skill in the art that the present invention may be practiced without these specific details. In other instances, well-known methods, procedures, components and structures may not have been described in detail so as not to obscure the present invention.

It will be appreciated that although part of the discussion heroin may relate, for exemplary purposes, to a heart, heart chambers and/or heart atriums, embodiments of the present invention are not limited in this regard, and may be used in conjunction with various other vessels, lumens, organs or body sites. For example some embodiments of the present invention may include regulating fluid transfer between cavities in the brain, between selected organs, between blood vessels (e.g., between the aorta and the vena-cava) etc., and/or between other suitable lumens, for example, zones, cavities, organs, vessels, regions or areas in a body.

Some embodiments of the present invention include, for example, a method and apparatus for controlling in-vivo pressure by reducing or otherwise controlling pressure differences between two or more body sites, for example, two chambers of the human heart (e.g., the left atrium and the right atrium). For example, such pressure control may be used to help solve the problem of increased cardiac filling pressure in patients with congestive heart failure and predominantly diastolic dysfunction, thereby helping to minimize or prevent pulmonary fluid accumulation, edema formation and clinical complaint of dyspnea. In another example the pressure control may be used to reduce left ventricle filling pressure. Some embodiments of the invention may include a Differential Pressure Regulation Device (DPRD), for example, including a shunt, tube or other structure having an orifice, tube or opening to fluidically connect two or more lumens, for example, to connect a left atrium of a heart with a right atrium of the heart. In accordance with some embodiments of the invention, the DPRD may include an adjustment mechanism or a regulation mechanism, able to adjust, modify or otherwise regulate, for example the cross-sectional area of the orifice, for example, in relation to a change in pressure difference between the first and second lumens, for example, such as to increase and/or decrease the flow-rate of blood between the two lumens.

Some embodiments of the present invention may be used, for example, to unload an excessive filling pressure of a left heart ventricle in a Congestive Heart Failure (CHF) patient, and to potentially prevent or reduce the occurrence of pulmonary edema.

Some embodiments of the present invention include, for example, implanting an adjustable DPRD in a wall between two heart chambers, e.g., between the left atrium and the right atrium. The pressure regulation device may, for example, allow a selective volume of blood to flow from the left atrium to the right atrium. In relation to the change in pressure difference between the left atrium and the right atrium. The pressure regulation device may, for example, be adjusted to selectively change the size or shape of the opening, amount of blood allowed to flow through, etc.

In some embodiments, the pressure regulation device may be configured to maintain a continual flow between two or more lumens, for example, between the left atrium and the right atrium. For example, a shunt, tube or other structure may be coupled to a cover, valve opening, valve stem, or other flow regulation mechanism that may be configured to be continually ajar, to enable a selected minimal quantity of fluid to continually flow between two lumens in a body, for example, between the heart chambers. The cover may be subsequently adjusted, for example may be further opened and/or closed, to control the quantity of fluid flow between the lumens. The fluid flow through the DPRD may increase or decrease in accordance with changes in the pressure or pressure difference between the two lumens. For example, cover may be opened and/or closed as the pressure in the left atrium increases or decreases relative to the pressure in the right atrium. In some embodiments the DPRD may be configured such that the orifice cover has no direct contact with the shunt opening to reduce help minimize or prevent tissue growth on or around the orifice cover. Such a configuration may enable a continuous fluid flow through the DPRD, and may help to prevent or reduce the occurrence of clotting or formation of biofilm or other unwanted growths. In some embodiments the DPRD may be used to flush or clean out the shunt and/or shunt cover etc.

Reference is made to FIG. 1A, which schematically illustrates a DPRD 101 implanted in a heart 109, in accordance with an exemplary embodiment of the present invention. DPRD 101 may be implanted between two or more body lumens, for example, between a left atrium 102 and a right atrium 103 of heart 102. DPRD 101 may be implanted in other heart chambers, using different arrangements of heart chambers, and/or in or between other body lumens. In some embodiments, an opening, puncture or other structure may be formed in a wall between two body lumens, for example, in septum 105 between left atrium 102 and right atrium 103, for example, using a puncturing or cutting device mounted to the distal end of a catheter or any other suitable puncturing mechanism. DPRD 101 may then be placed in a puncture using a catheter or another suitable delivery mechanism. In some embodiments, one or more tissue fixation elements, for example, support arms 106 may support DPRD 101 at a desired position in a generated hole or puncture.

DPRD 101 may include, for example, an adjustable shunt, tube or pathway 122 to enable fluids to flow between two body lumens, organs, regions or zones etc., for example between a left atrium 102 and a right atrium 103. DPRD 101 may include a Flow Regulation Mechanism (FRM) 108 as described herein, for example a flow valve, cover, valve opening, valve stem, or lid, to enable selected modification of the parameters of shunt 122, for example, by changing the cross section of the opening of shunt 122 or the shunt's shape etc., thereby regulating the blood flow from left atrium 102 to right atrium 103. In some embodiments FRM 108 may be set in a continually ajar position to enable a continual flow of blood between the left atrium and the right atrium. For example, FRM 108 may be purposefully left ajar, to enable a selected quantity of blood to continually flow between the heart chambers. FRM 108 may be subsequently adjusted, for example, by selectively changing the size or shape of the opening, amount of blood allowed to flow through, etc., to enable the area around the opening of shunt 122 and FRM 108 to be limited and/or expanded, thereby affecting effective flow-through of shunt 122, and enabling the quantity of blood flow between the chambers to be controlled. DPRD 101 may include one or more control mechanisms 110, for example, wires, springs, cords etc. to enable FRM 108 to be passively and/or actively controlled. In one embodiment springs may be used to enable FRM 108 to act in accordance with changes in differential pressure, for example, by being pre-loaded with a selected tension, to respond in a controlled way to changes in one or more pressure thresholds.

FRM 108 may be configured to respond to selective pressure profiles, thereby providing a known pressure relief profile. For example, FRM 108 may be preset, pre-calibrated and/or pre-configured to change its setting, adjust its configuration or position, and/or change the orifice width or flow amount etc., in accordance with changes in pressure difference between the left and right atriums of the heart. FRM 108 may be continually adjustable, for example to a continuously variable setting, for example in response to environmental conditions and/or external controls. In at least these ways, DPRD 101 may provide a selected, predictable and/or guaranteed flow of fluid between two or more bodily lumens or regions etc. In some embodiments the resting or default setting, opening size, flow level or position of FRM 108 may be changed, for example, according to pre-programmed parameters and/or remote control mechanisms. In some embodiments a continuously open or ajar FRM 108 may help prevent occlusion of shunt 122.

In some embodiments, below a certain pressure or pressure differential, the valve or device may be fully closed; however in other embodiments, below a certain pressure or pressure differential, the valve may be not fully closed or slightly ajar. For example, the valve may have a minimum opening size.

In some embodiments, one or more properties of the DPRD, for example, the size of the cross-section opening of the pressure regulation device, may be dependent on the blood pressure difference between the left atrium and the right atrium. Therefore, in some embodiments, the blood flow between the left atrium and the right atrium may be influenced by the change in blood pressure difference between the left atrium and the right atrium.

A DPRD according to some embodiments of the invention may allow for a reduction in ventricular pressure by reducing pressure in an atrium of the heart.

In some embodiments, a DPRD may be used for Atrium Septum Defect (ASD) patients, for example who may not be able to tolerate a complete uncontroiled atrium closure procedure, to selectively close a hole or gap in the septum.

In some embodiments, a DPRD may be used to transfer fluid from the left atrium to the right atrium, for example, to aid a patient with pulmonary hypertension. In such cases the DPRD may be positioned with FRM 108 in the left atrium. According to some embodiments of the present invention, FRM 108 may be unidirectional or bi-directional.

In some embodiments, a plurality of DPRD's may be implanted in a wall or other structure, for example, to help provide redundancy, to implant devices with different set ranges to achieve a higher level of opening control, and/or to enable adding of additional devices. Implanting a plurality of DPRD's may enable the delivering catheter diameter to be reduced, as two or more DPRD's of a lesser diameter may be delivered.

In other embodiments FRM 108 may include a cover, lid or other suitable mechanism that may have various forms to enable partial or total closure of FRM 108. Reference is now made to FIGS. 1B-1G. In FIG. 1B FRM 108 may include two or more arms 120 which may be configured to be continuously or constantly ajar at opening 125 of shunt 122. For example, FRM 108 may be configured to remain continually at least partially detached from shunt 122, to allow a continuous flow of fluid between left atrium 102 and right atrium 103. Arms 120 may be further opened and/or closed in response to changes in pressure differences between the heart chambers. Arms 120 may be constructed from a flexible polymer or other suitable materials. Arms 120 may have rounded shapes at arm ends 130, for example, to help prevent blood stagnation.

In FIG. 1C FRM 108 may include a shunt 122, and two or more flexible membranes 135, which may be configured to be constantly ajar at opening 125 to enable a continuous blood flow through shunt 122. For example, in the various embodiments discussed herein, a device may be set so that no matter what the pressure or pressure differential between chambers, a minimum opening size may be set or flow amount may occur. Membrane 135 may include at least one spring-type mechanism, to help expand and/or contract membrane 135, in response to changes in pressure differences between the heart chambers.

Figure 1E:
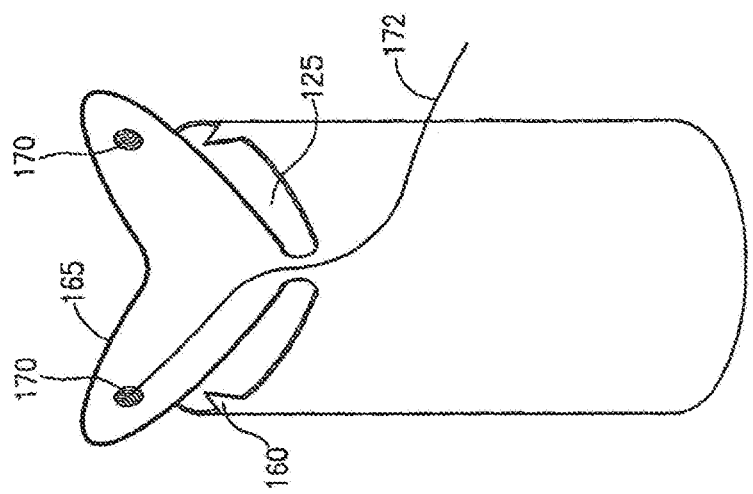
Figure 1D:
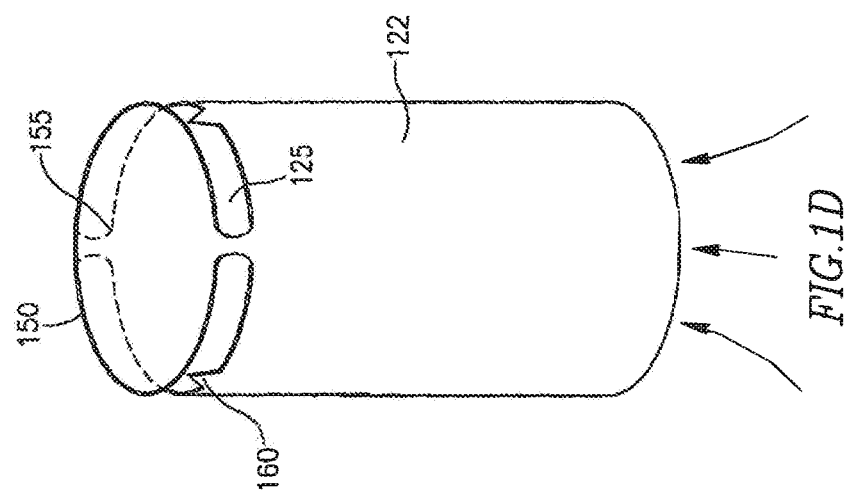

In FIG. 1D FRM 108 may include a shunt 122, and one or more flexible or spring based lid, membrane or leaflets 150, optionally connected to shunt 122 by a spring or other suitable pressure sensitive mechanism 155. In one embodiment pressure sensitive mechanism 155 may be pre-loaded to respond in a controlled way to changes in one or more pressure thresholds. Lid 150 may be configured to be constantly ajar at opening 125 to enable a continuous blood flow through shunt 122. FRM 108 may include one or more raised areas 160, for example, thorn shaped objects or objects with other suitable shapes to help prevent lid 150 from making full contact with shunt 122.

In FIG. 1E FRM 108 may include a shunt 122, and one or more angled flexible membranes or leaflets 165, which may be configured to be constantly ajar at opening 125 to enable a continuous blood flow through shunt 122. In one embodiment leaflets 165 may be pre-loaded with a selected tension to respond in a controlled way to changes in one or more pressure thresholds. Leaflet 165 may include at least one spring mechanism or other suitable mechanism to help close and/or open leaflet 165 in response to changes in pressure differences between the heart chambers. Leaflet 165 may include at least one magnet or electromagnet 170 or other suitable mechanism to help remotely close and/or open leaflet 165. A conducting wire 172 or other suitable mechanism may be used to activate magnet(s) or electromagnet(s) 170.

Figure 1G:
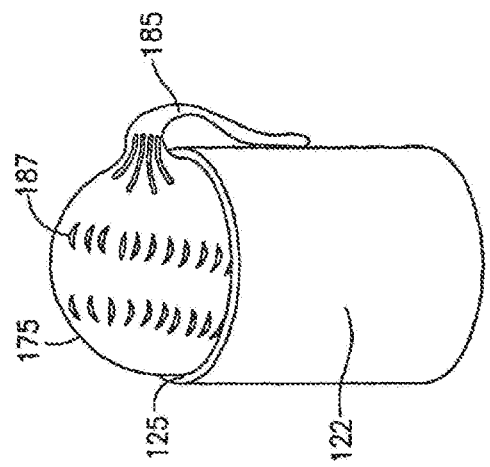
Figure 1F:
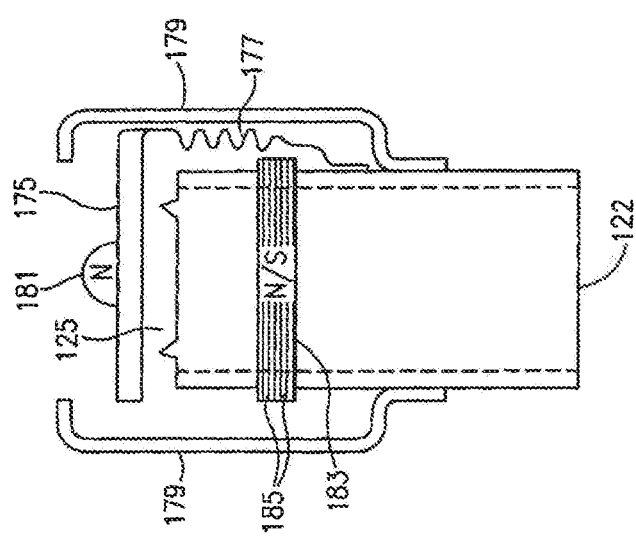

In FIG. 1F FRM 108 may include a shunt 122, and a cap, valve opening, valve stem, or other mechanism 175, which may be configured to be constantly ajar at opening 125 to enable a continuous blood flow through shunt 122. Cap 175 may be coupled to a spring 177 or other suitable pressure sensitive mechanism. In one embodiment spring 177 may be pre-loaded with a selected tension to respond in a controlled way to changes in one or more pressure thresholds. FRM 108 may include one or more cap motion limiters 179. FRM 108 may include a fixed polarized magnet 181 and an electromagnetic coil 183 that includes one or more conductors 185. Cap 175 may be opened and/or closed in response to changes in pressure differences between the heart chambers and/or by remotely activating magnet 181 and/or magnetic coil 183. For example, when magnet 181 is activated cap 175 may be further opened, and when coil 183 is activated cap 175 may be further closed.

As shown in FIG. 1G FRM 108 may include a shunt 122, and a cap 175, which may be configured to be constantly ajar at opening 125 to enable a continuous blood flow through tube 122. Cap 175 may be connected to shunt 122 by a connection arm 185. Cap 175 may include cuts, slots, grooves or slits etc. 187 to enable a continuous blood flow through shunt 122. Slots 187 may be of different sizes, depths, widths, or densities, which may help dictate whether various areas of cap 175 are to be stronger and less flexible or weaker and more flexible, and may therefore respond differently to changes in pressure differences between the bodily lumens. For example, in an area where there are more or deeper incursions the area may be relatively weak and flexible, thereby allowing cap 175 to be at least partially opened by a relatively low pressure blood flow through shunt 122. In an area where there are fewer and/or more superficial Incursions the area may be relatively strong or less flexible, thereby only allowing cap 175 to be at least partially opened by a relatively high pressure blood flow through shunt 122.

Figure 1H:
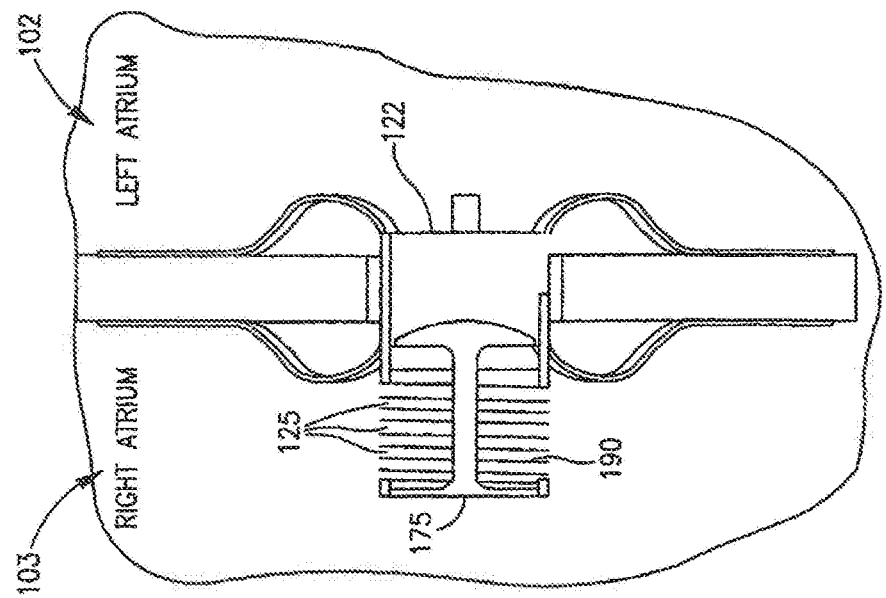
Figure 1I:
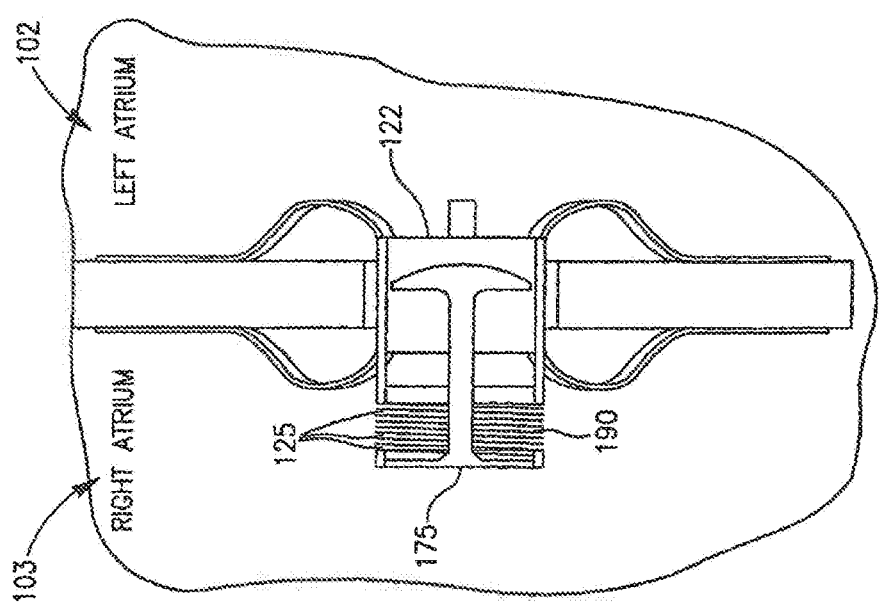

As shown in FIGS. 1H and 1I FRM 108 may include a shunt 122, and a cap 175, which may be configured to be constantly ajar at opening 125 to enable a continuous blood flow through shunt 122. Cap 175 may be coupled to a spring 190 or other suitable pressure sensitive mechanism. Spring 190 and cap 175 may be connected to a piston or pump mechanism 192. As can be seen in FIG. 1I, cap 175 may be opened and/or closed In response to changes in pressure differences between the heart chambers and/or by piston 192 activating spring 190 to extend and/or distend cap 175, thereby changing the size of opening(s) 125.

Figure 1J:
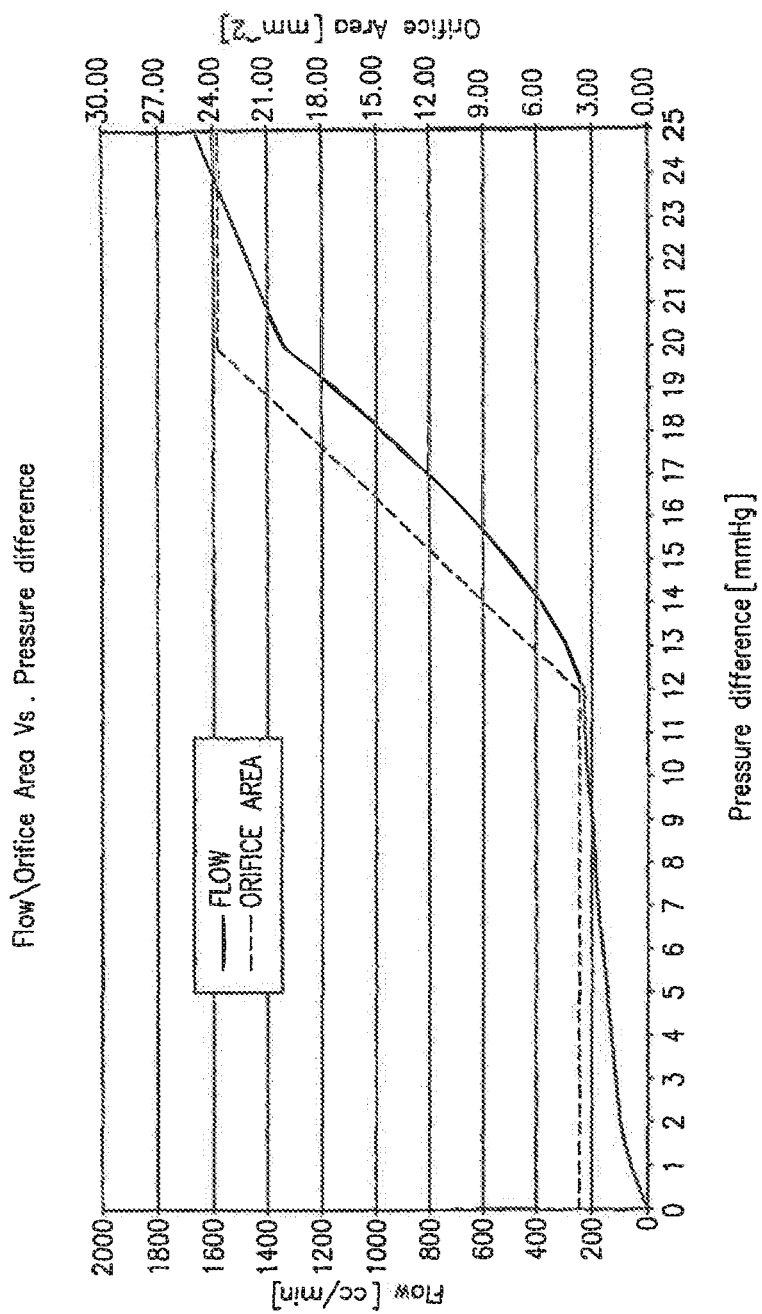
FIG. 1J is a chart describing an example of a pressure curve related to the relationship between the change in pressure difference between two lumens, the flow through the flow control mechanism and the orifice area, in accordance with an exemplary embodiment of the present invention.

According to some embodiments of the present invention, the usage of DPRD 101 may enable generation of a pressure curve related to the relationship between the change in pressure difference between two lumens, the flow through the flow control mechanism and the orifice area. Any required or selected design parameters may be used. Reference is now made to FIG. 1J, which illustrates an example of such a pressure curve. As can be seen in FIG. 1J, below a pressure differential of 12 mmHg, the opening or orifice size may be relatively stable, and flow may be influenced substantially by the pressure difference. When pressure difference rises above approximately 12 mmHg until approximately 20 mmHg the flow may increase at a higher rate, as it may now be influenced by both the increase in orifice area and the increase in pressure difference. When pressure difference rises above approximately 20 mmHg the flow rate increase at a slower rate, since the orifice area may have already reached its maximum cross-section, and the flow may be influenced substantially by the pressure difference. Pressure differences and/or may be effected by linear and/or non-linear changes in the orifice area. Other pressure difference, flow and/or orifice area levels, relationships, and interrelationships may be used, as may other parameters, variables, minimum and maximum limits etc.

Reference is made to FIGS. 2A and 2B, which schematically illustrate a cross-section view and a side view, respectively, of an adjustable DPRD 201 in accordance with an exemplary embodiment of the invention. DPRD 201 may include, for example, a frame 220 connected to one or more support arms, e.g., arms 211-216. Frame 220 may include, for example, a flexible fixation frame, ring or tube. Frame 220 may be formed from a flexible material, for example, a flexible metal, super elastic alloy, and/or a shape-memory material, e.g., Nitinol or other suitable materials.

Although DPRD 201 is described herein as having six arms or appendages 211-216, for exemplary purposes, embodiments of the present invention are not limited in this regard and may include a different number of arms, for example, one arm, two arms, ten arms, or the like.

Arms or appendages 211-216 may be flexible and/or may be pre-shaped to achieve a desired functionality. For example, arms 211-216 may be folded during an insertion process, e.g., inside a suitable delivery tube. In some embodiments, arms 211-216 may be formed of a super elastic material, for example, a Shape-Memory Alloy (SMA), e.g., nickel-titanium (NiTi) alloy. Other suitable materials may include, for example, metals, stainless steel, and/or other suitable materials. At least part of arms 211-216 or other selected elements of DPRD 201 may be coated and/or textured to increase their bio-compatibility and/or to increase the degree to which these elements may become selectively endothelialized, as may be desired in some implantation conditions.

DPRD 201 may include, for example, a FRM 250, for example, including a cover, valve opening, valve stem, or other flow regulation mechanism with one or more pre-set positions, to selectively cover an orifice resulting from the deployment of DPRD 201. FRM is described in detail below.

As illustrated schematically in FIG. 2B, DPRD 201 may have two sides, which may be referred to herein as a proximal side 251 and a distal side 252, respectively. For example, DPRD 201 may be implanted in heart 109, such that the proximal side 251 of DPRD 201 may face the right atrium 103, and the distal side 252 of DPRD 201 may face the left atrium 102. Other orientations of sides 251 and 252 may be used, as may other numbers of sides.

In some embodiments, the distal side 252 of DPRD 201 may be connected to a distal set of arms or appendages, e.g., arms 211-213, and the proximal side 251 of DPRD 201 may be connected to a proximal set of arms or appendages, e.g., arms 214-216. Thus, when DPRD 201 is implanted in heart 109, the distal set of arms 211-213 may first be discharged in the left atrium 102, e.g., to the right of septum 105 in FIG. 1, thus supporting DPRD 201 to the left side, from the patient's perspective, of septum 105. Then, as the insertion of DPRD 201 is completed, e.g., by retracting a catheter or delivery tube carrying DPRD 201, the proximal set of arms 214-216 may be discharged in the right atrium 103, e.g., to the left of septum 105 in FIG. 1, thus supporting the right side, from the patient's perspective, of septum 105. In this manner, arms 211-216 may support frame 220 of DPRD 201 at a desired position between the left atrium 102 and the right atrium 103.

Figure 3:
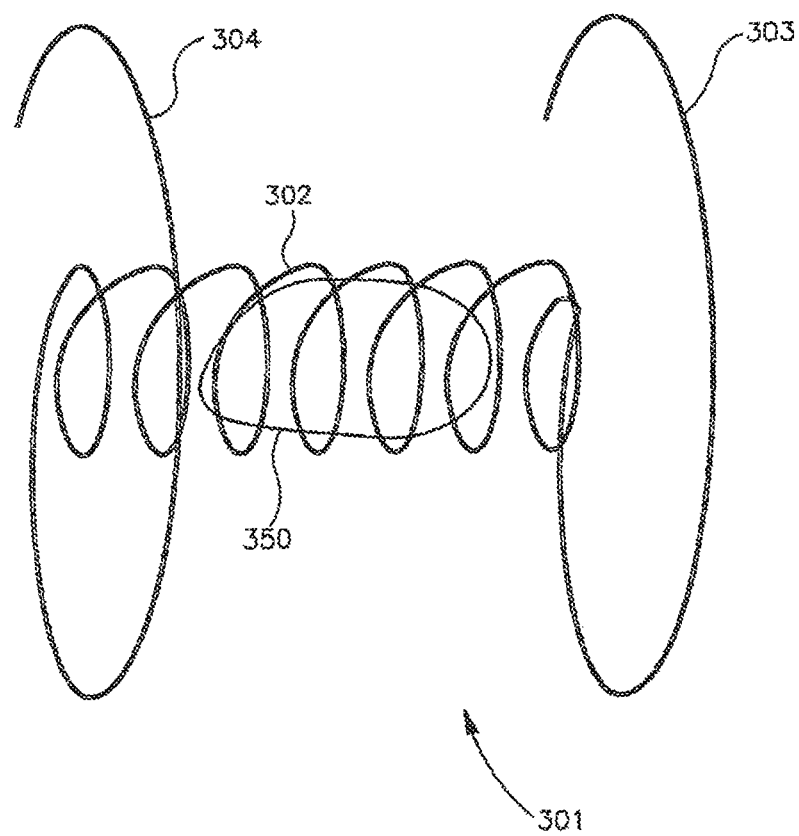
FIG. 3 is a schematic illustration of a shunt in accordance with another exemplary embodiment of the invention.

Reference is now made to FIG. 3, which schematically illustrates a DPRD 301 in accordance with another exemplary embodiment of the present invention. DPRD 301 may include, for example, a frame 302 connected to one or more arms or appendages, for example, arms 303 and 304.

Frame 302 may include, for example, a flexible fixation frame formed from a flexible material, for example, a flexible metal, e.g., Nitinol or Nitinol wire. Frame 302 may have a generally helical shape, for example, as schematically illustrated in FIG. 3, and may be integrally formed with curved arms 303 and 304 at either end of frame 302, as schematically illustrated in FIG. 3. Other suitable shapes may be used. Arms 303 and 304 may be flexible and may be pre-shaped to achieve a desired functionality. For example, arms 303 and 304 may be folded during an Insertion process, e.g., inside a suitable delivery tube, in order to be subsequently discharged for positioning the frame 302 in a puncture. In accordance with some exemplary embodiments of the present invention, DPRD 301 may include a FRM 350, for example, a FRM as detailed herein.

Figure 4:
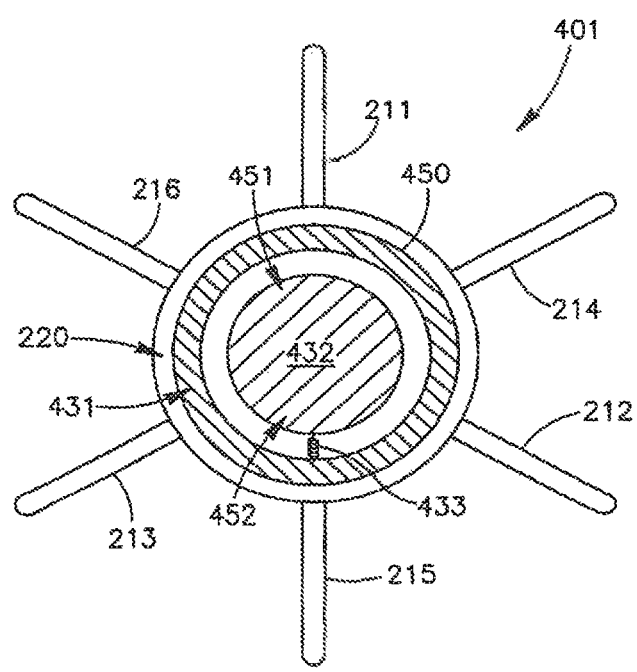
FIG. 4 is a schematic illustration of a shunt including a Flow Regulation Mechanism (FRM) in accordance with an exemplary embodiment of the invention.

Reference is also made to FIG. 4, which schematically illustrates a DPRD 401 including a DPRD 450 in accordance with an exemplary embodiment of the invention. DPRD 450 may be an example of FRM 250 or FRM 350. For exemplary purposes only, DPRD 450 is shown in conjunction with a DPRD 401 which may be similar to DPRD 201, although DPRD 450 may be used in conjunction with DPRD 301 or any other suitable shunts or medical devices.

DPRD 450 may include, for example, a disk 432 connected to a ring 431 by a spring 433. Disk 432 may be formed of a bio-compatible material, for example, pyrolitic carbon or stainless steel. Spring 433 may include one or more swivel springs, twisting springs, or any other spring elements, which may hold disk 432 inside ring 431 when there is substantially no pressure differential between the two sides of DPRD 401, e.g., between the proximal side 251 and the distal side 252 of DPRD 201 of FIG. 2B.

In response to a pressure differential between the two sides of DPRD 401, disk 432 may move away from the atrium having the relatively higher pressure, typically the left atrium, bending spring 433 which may apply a counterforce to the movement of disk 432, thereby opening and/or enlarging a cavity through which blood may pass. The counterforce applied by spring 433 may depend on the pressure differential between the two sides of DPRD 401, for example when the pressure in an atrium forces spring 433 to contract, such that the higher the pressure differential across DPRD 401, the larger the opening to allow relief of such pressure differential by flow from the high pressure side to the low pressure side. In this manner, the pressure differential between the proximal and distal sides of DPRD 401 may be controlled in accordance with one or more selected levels. In some embodiments the various configurations for DPRDs described herein may allow for opening sizes or flow rates that vary continuously with pressure differentials.

It will be appreciated that when there is substantially no pressure difference between the two sides of DPRD 401, or when the pressure difference is relatively small, disk 432 may be fully closed, or in addition may not entirely block the flow of blood through DPRD 450, for example, through the area between disk 432 and ring 431. For example, disk 432 may be selectively set with a gap between ring 431 and disk 432, such that disk 432 may function as a leaking valve to enable blood to continuously flow through a puncture. The continual freedom of flow across DPRD 401 may, for example, prevent blood clotting and/or thrombus formation in and/or around disk 432.

In some embodiments, ring 432 may be asymmetric, for example, ring 432 may have a relatively wider upper section 451 and a relatively narrower lower section 452. This may allow, for example, blood passage at a relatively small flow-rate during tilting of disk 432 under increased pressure, until disk 432 bends beyond the upper section of ring 431, thereby providing a pressure or pressure differential threshold at which the valve opens or begins to open, to increase the blood flow cross-section through the vessel. The pressure threshold may be a continual (e.g., infinitely variable) set of pressure points at which the valve opens or allows a pressure flow in accordance with the pressure. For example, the valve may remain closed or slightly ajar until a certain pressure, then above that pressure open continually until an upper pressure is reached, at which the valve is fully open. It is noted that an asymmetric ring 432 or other asymmetric components may be used to achieve similar functionality in various other FRMs, DPRDs, shunts and/or devices in accordance with embodiments of the present invention.

In some embodiments, ring 431 may be formed of, for example, a suitable metal. In some embodiments, ring 431 may be Integrated within frame 220, or ring 431 and frame 220 may be implemented using an integrated ring-frame component. Ring 431 and/or frame 220 may be formed of a suitable wire or tube. Ring 431 and/or arms 211-216 may be formed of a suitable wire or tube, e.g., the same wire or tube and/or the same material.

Figure 5:
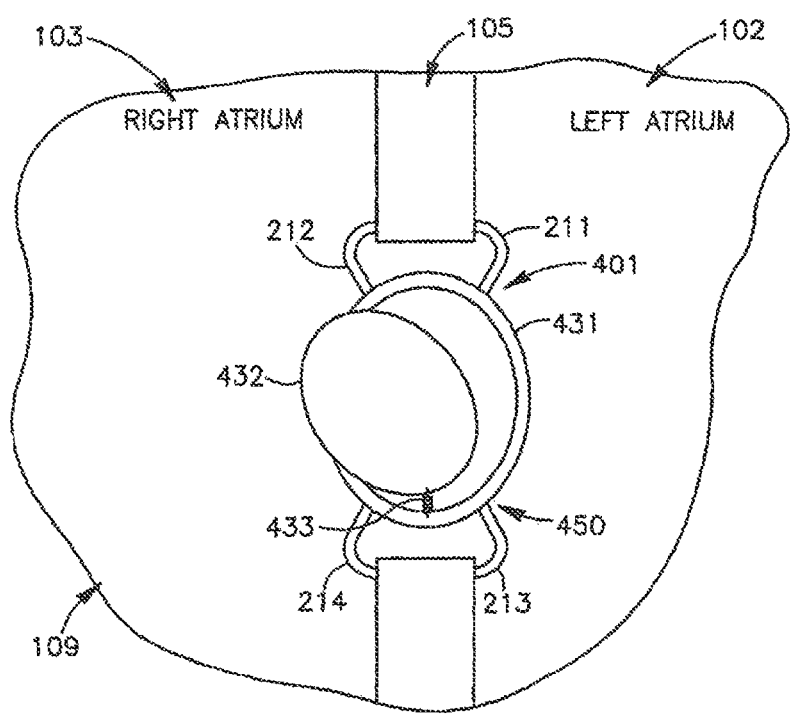
FIG. 5 is a schematic illustration of the shunt of FIG. 4 and incorporating a FRM in an open state in accordance with an exemplary embodiment of the invention.

Reference is also made to FIG. 5, which schematically illustrates DPRD 401 implanted in heart 109, incorporating DPRD 450 in an open state in accordance with an exemplary embodiment of the present invention. A pressure difference may exist between left atrium 102 and right atrium 103, for example, the pressure in left atrium 102 may be larger than the pressure in right atrium 103. The pressure difference may cause disk 432 to move towards right atrium 103 and bend the spring 433, thereby creating an enlarged opening through which more blood may flow from left atrium 102 to right atrium 103. As the blood flows towards right atrium 103, the pressure in left atrium 102 may decrease and the pressure in the right atrium may increase, thereby reducing the pressure difference between the left atrium 102 and the right atrium 103, and allowing spring 433 to pull back disk 432 towards a closed or substantially closed position. Other mechanisms to enable disk 432 to move may be used.

Figure 6:
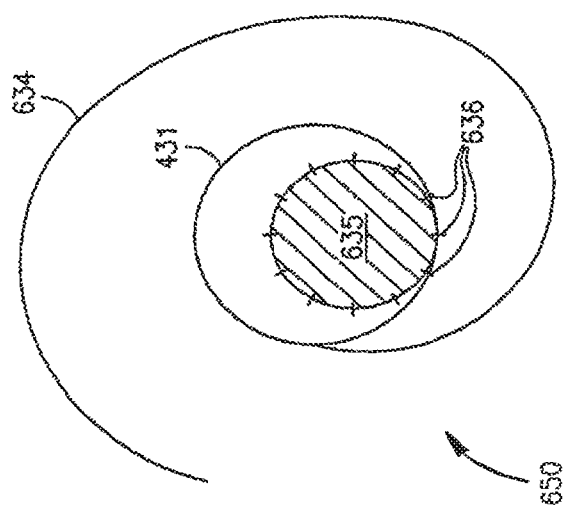
FIG. 6 is a schematic illustration of a FRM in accordance with another exemplary embodiment of the invention, which may be used, for example, in conjunction with the DPRD of FIG. 1, the shunt of FIGS. 2A-2B, or the shunt of FIG. 3.

FIG. 6 schematically illustrates a DPRD 650 in accordance with another exemplary embodiment of the invention. DPRD 650 may be an example of FRM 108, FRM 250 or FRM 350. DPRD 650 may include, for example, ring 431 and a pre-shaped wire 634. Wire 634 may include a flexible metal wire, for example, formed of Nitinol or other suitable materials. In one embodiment wire 634 may be curved to a shape of a horse-shoe or tongue or another suitable shape. In some embodiments, an end of wire 634 may be attached to ring 431, or wire 634 and ring 431 may be formed of the same wire, tube or other suitable material.

Wire 634 may be covered by or connected to a cover or sheet 635, which may include, for example, a flat sheet of bio-compatible material, for example, a biological tissue material used in conjunction with artificial valve leaflets. Sheet 635 may be attached to wire 634, for example, using one or more stitches 636.

DPRD 650 may be included in, for example, DPRD 201 or DPRD 301, implanted in heart 109. A pressure difference may exist between left atrium 102 and right atrium 103, for example, the pressure in left atrium 102 may be larger than the pressure in right atrium 103. The pressure difference may cause sheet 635 to move, utilizing the elasticity of wire 634, thereby creating a cavity through which blood may flow from left atrium 102 to right atrium 103. As the blood flows in that direction, the pressure in left atrium 102 may decrease and the pressure in the right atrium may increase, thereby reducing the pressure difference between the left atrium 102 and the right atrium 103, and allowing sheet 635 to move back towards a closed or substantially closed position or towards a position wherein sheet 635 is in a marginally opened position.

It is noted that when there is no pressure difference between the left atrium 102 and the right atrium 103, or when the pressure difference is relatively small, sheet 635 may not entirely block a blood flow through DPRD 650, for example, through the area around sheet 635, or between sheet 635 and ring 431. This may, for example, prevent blood clotting and/or thrombus formation in and/or around sheet 635 or DPRD 650. However, as with the other configurations discussed herein, in other embodiments, the opening or valve may be completely closed at certain pressure differentials.

Figure 7:
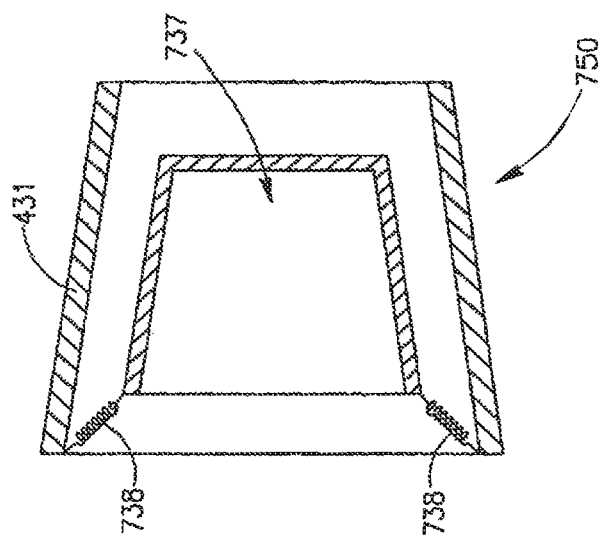
FIG. 7 is a schematic illustration of a FRM in accordance with another exemplary embodiment of the invention, which may be used, for example, in conjunction with the DPRD of FIG. 1, the shunt of FIGS. 2A-2B, or the shunt of FIG. 3.

FIG. 7 schematically illustrates a FRM 750 in accordance with another exemplary embodiment of the invention. FRM 750 may include, for example, ring 431 connected to a cone 737 using one or more springs 738. Cone 737 may be positioned inside ring 431, and may be formed of, for example, a bio-compatible material, e.g., pyrolitic carbon or stainless steel. Cone 737 may have a suitable shape, for example, rectangular, square-shaped, circular, oval, trapezoid-shaped, cone-shaped, or other suitable shapes.

FRM 750 may be included in a shunt, e.g., DPRD 201 or DPRD 301, implanted in heart 109. Springs 738 may include one or more compression springs, and may hold cone 737 inside ring 431, for example, when substantially no pressure difference exists between left atrium 102 and right atrium 103.

When a pressure difference exists between left atrium 102 and right atrium 103, for example, when the pressure in left atrium 102 is larger than the pressure in right atrium 103. FRM 750 may allow blood flow from left atrium 102 to right atrium 103. The pressure difference may cause cone 737 to move back against springs 738, thereby opening or enlarging a cavity through which blood may flow from left atrium 102 to right atrium 103. As the blood flows in that direction, the pressure in left atrium 102 may decrease and the pressure in the right atrium may increase, thereby reducing the pressure difference between the left atrium 102 and the right atrium 103, and allowing cone 737 to move back towards a closed or substantially closed position.

It is noted that when there is no pressure difference between the left atrium 102 and the right atrium 103, or when the pressure difference is relatively small, cone 737 may not entirely block a blood flow through FRM 750, for example, through the area around cone 737, or between cone 737 and ring 431. This may, for example, prevent blood clotting and/or thrombus formation in and/or around cone 737 or FRM 750.

Figure 8:
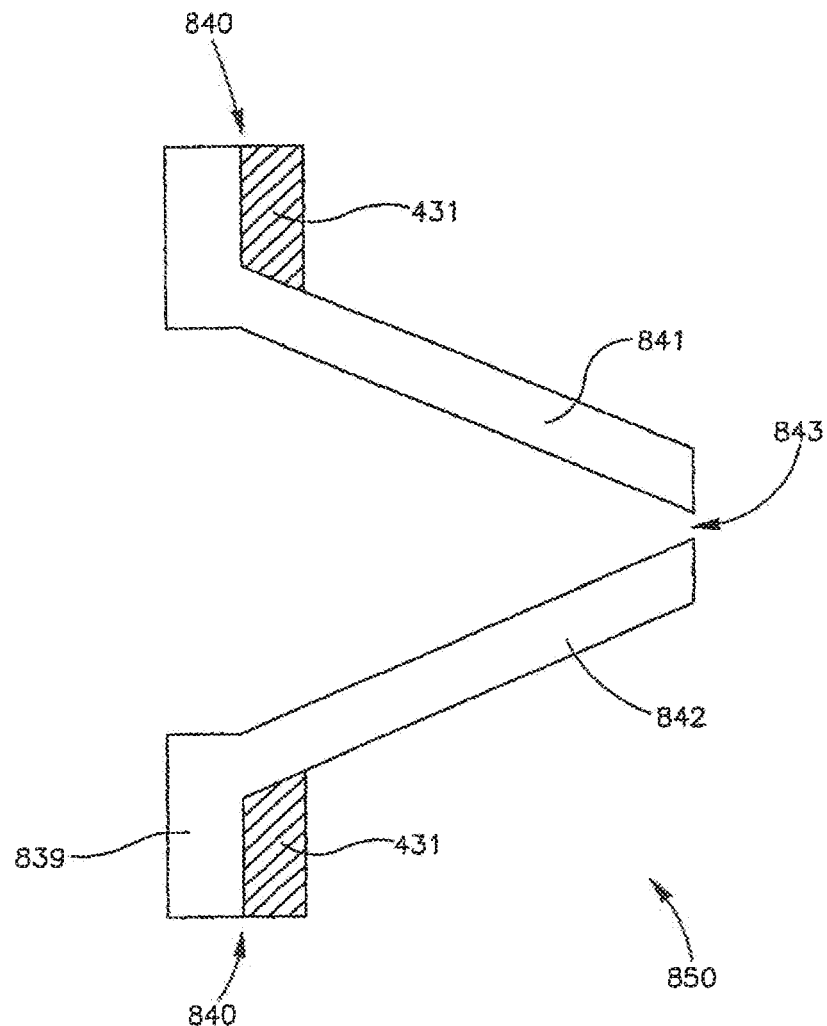
FIG. 8 is a schematic illustration of a FRM in accordance with another exemplary embodiment of the invention, which may be used, for example, in conjunction with the DPRD of FIG. 1, the shunt of FIGS. 2A-2B, or the shunt of FIG. 3.

FIG. 8 schematically illustrates a FRM 850 in accordance with another exemplary embodiment of the invention. FRM 850 may include, for example, a flexible valve 839 connected to and positioned inside ring 431. Valve 839 may be formed of, for example, a bio-compatible material, e.g., polyurethane or silicone. Valve 839 may be attached to ring 431, for example, by gluing or stitching a base 840 of valve 839 inside ring 431. Valve 839 may include one or more leaflets, for example, leaflets 841 and 842 able to move and create or enlarge an opening 843. In some embodiments, the size of opening 843 may be in relation to a pressure applied to leaflets 841 and 842.

FRM 850 may be included in a shunt, tube or conduit, e.g., DPRD 201 or DPRD 301, implanted in heart 109. When a pressure difference exists between left atrium 102 and right atrium 103, for example, when the pressure in left atrium 102 is larger than the pressure in right atrium 103, FRM 850 may allow blood flow from left atrium 102 to right atrium 103. The pressure difference may stretch, spread or push leaflets 841 and/or 842, thereby increasing the distance between them and enlarging the opening 843, through which blood may flow from left atrium 102 to right atrium 103. As the blood flows in that direction, the pressure in left atrium 102 may decrease and the pressure in the right atrium may increase, thereby reducing the pressure difference between the left atrium 102 and the right atrium 103, and allowing leaflets 841 and/or 843 to move back towards a closed or substantially closed position.

It is noted that when there is no pressure difference between the left atrium 102 and the right atrium 103, or when the pressure difference is relatively small, valve 839 and leaflets 841 and 842 may not entirely block a blood flow through FRM 850, for example, through the opening 843. This may, for example, prevent blood clotting and/or thrombus formation in and/or around valve 839 or FRM 850.

Figure 9:
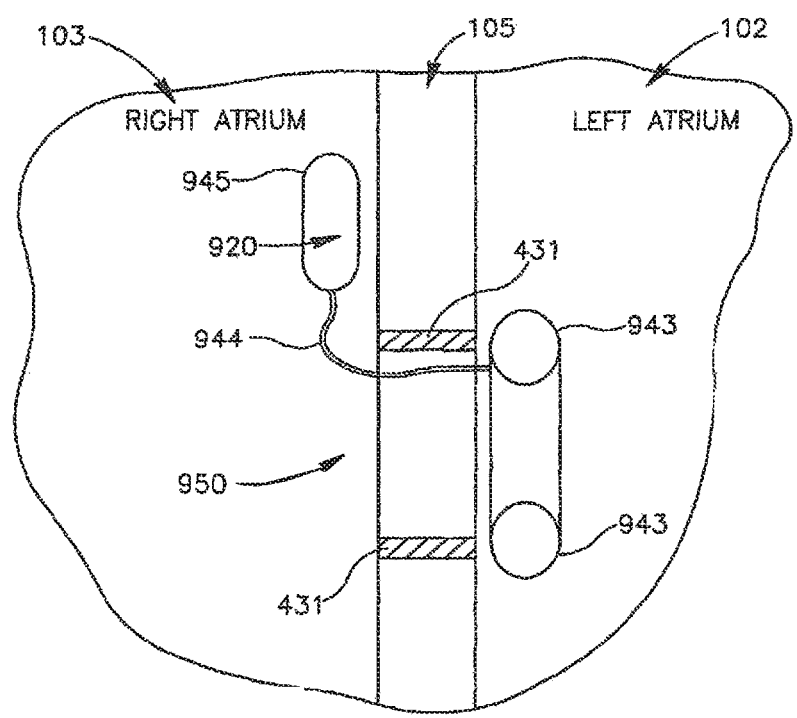
FIG. 9 is a schematic illustration of a FRM within a heart, in accordance with another exemplary embodiment of the invention.

FIG. 9 schematically illustrates a DPRD 950 within heart 109, in accordance with another exemplary embodiment of the invention. DPRD 950 may include a plurality of balloons or sacs inter-connected through one or more tubes, for example, a non-compliant balloon 943 connected through a tube 944 to a compliant balloon 945. The non-compliant balloon 943 may be placed in the left atrium 102 and/or in a puncture, and the compliant balloon 945 may be placed in the right atrium 103. In some embodiments, balloons 943 and/or 945 may be may be attached to a ring (e.g., ring 431). In some embodiments balloons 943 and/or 945 may contain a liquid 920.

Liquid 920 may flow from balloon 943 to balloon 945 or vice versa, for example, in relation to a pressure difference between the left atrium 102 and the right atrium 103. For example, when there is a relatively larger pressure in the left atrium 102, liquid 920 may flow from non-compliant balloon 943 through tube 944 to compliant balloon 945, thereby deflating the non-compliant balloon 943 and inflating the compliant balloon 945. It is noted that compliant balloon 945 may be more flexible than non-compliant balloon 943, allowing the compliant balloon 945 to act as a spring mechanism to control the deflating of the non-compliant balloon 943.

Figure 10:
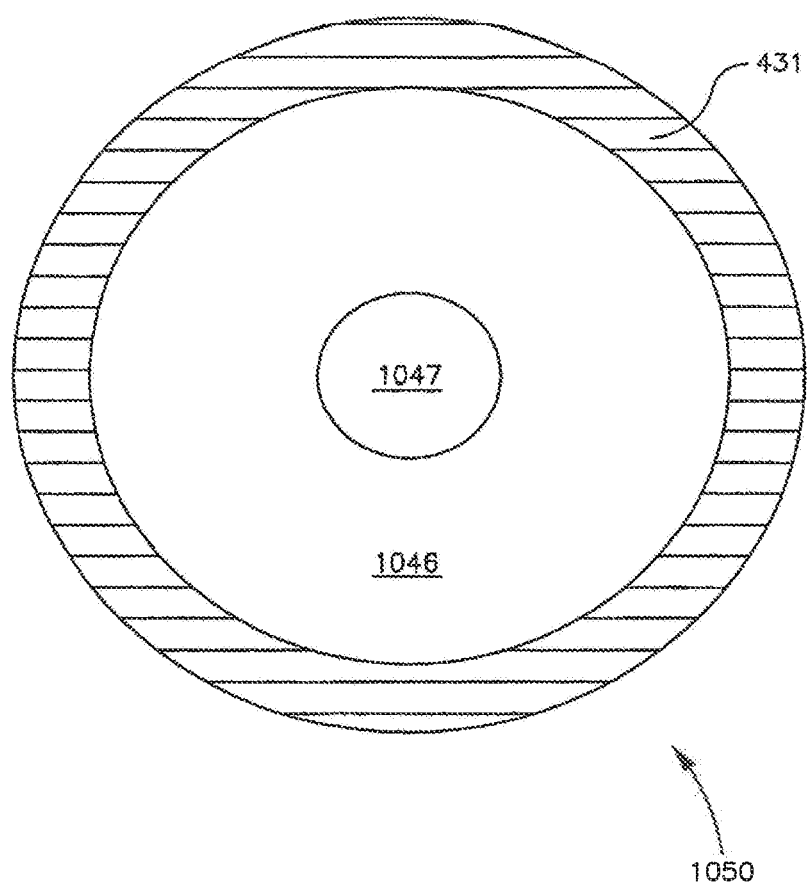
FIG. 10 is a schematic illustration of a FRM in accordance with another exemplary embodiment of the invention, which may be used, for example, in conjunction with the DPRD of FIG. 1, the shunt of FIGS. 2A-2B, or the shunt of FIG. 3.

FIG. 10 schematically illustrates a DPRD 1050 in accordance with another exemplary embodiment of the invention. DPRD 1050 may include, for example, ring 431 and a flexible disk 1046 having a hole 1047. In some embodiments, hole 1047 may be substantially circular and may be located, for example, substantially in the center of flexible disk 1046. Flexible disk 1046 may be formed of, for example, a flexible polymetric material, e.g., silicone rubber or polyurethane.

DPRD 1050 may be implanted in heart 109, and hole 1047 may change its diameter in relation to a pressure difference between the left atrium 102 and the right atrium 103. For example, the pressure difference may push backwards or stretch the flexible disk 1046, thereby enlarging the hole 1047 and allowing a larger area through which blood may flow from the left atrium 102 to the right atrium 103.

It is noted that when there is no pressure difference between the left atrium 102 and the right atrium 103, or when the pressure difference is relatively small, hole 1047 may still be open and may have a relatively small diameter, and flexible disk 1046 may not entirely block a blood flow through DPRD 1050. This may, for example, prevent blood clotting and/or thrombus formation in and/or around DPRD 1050.

Figure 11:
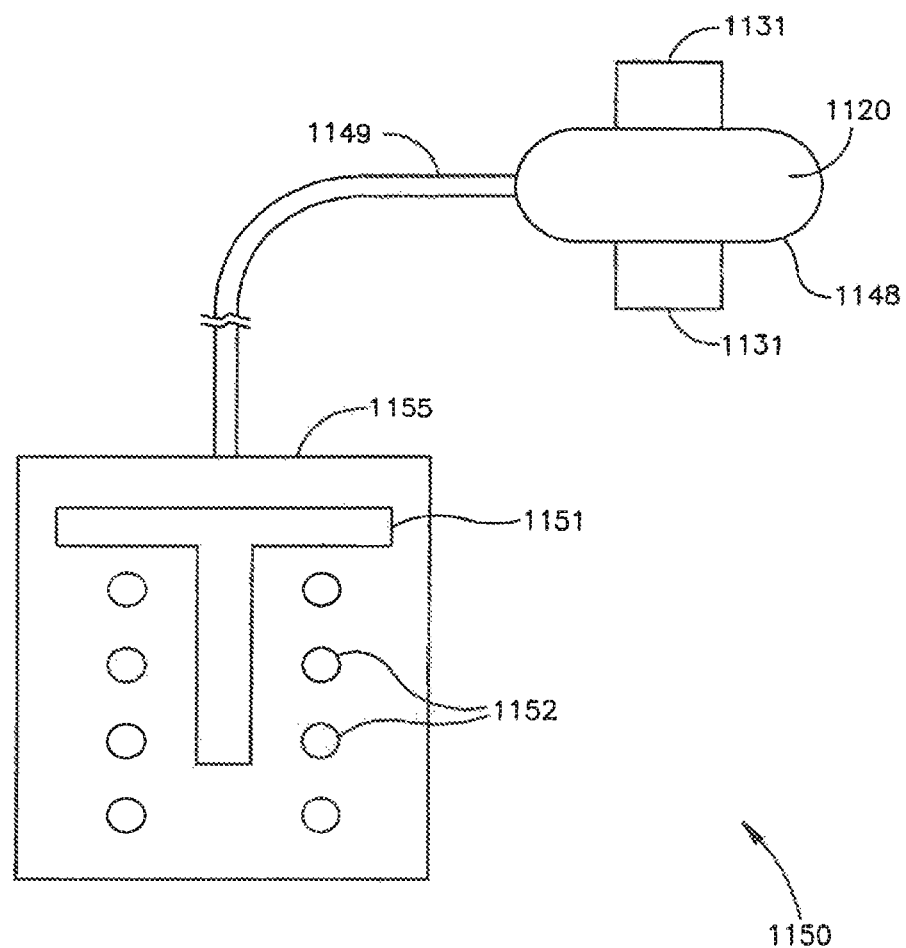
FIG. 11 is a schematic illustration of a FRM in accordance with another exemplary embodiment of the invention, which may be used, for example, in conjunction with the DPRD of FIG. 1, the shunt of FIGS. 2A-2B, or the shunt of FIG. 3.

FIG. 11 schematically illustrates a DPRD 1150 in accordance with another exemplary embodiment of the invention. DPRD 1150 may include, for example a balloon or sac 1148 such as a non-compliant balloon containing a liquid 1120. The balloon 1148 may be placed or connected inside a ring 1131, which may include, for example, a ring similar to ring 431 and/or a frame. A tube 1149 may connect balloon 1148 to a reservoir 1155, which may include one or more pistons 1151 able to move against one or more compression springs 1152. Springs 1152 may be formed of, for example, metal or a suitable elastic material.

DPRD 1150 may be implanted in heart 109, and balloon 1148 may change its volume in relation to a pressure difference between the left atrium 102 and the right atrium 103. For example, the pressure difference may push or deflate the balloon 1148, thereby causing liquid 1120 to flow from balloon 1148 to reservoir 1155. This may create or enlarge an opening inside ring 1131, through which blood may flow from the left atrium 102 to the right atrium 103.

Figure 12:
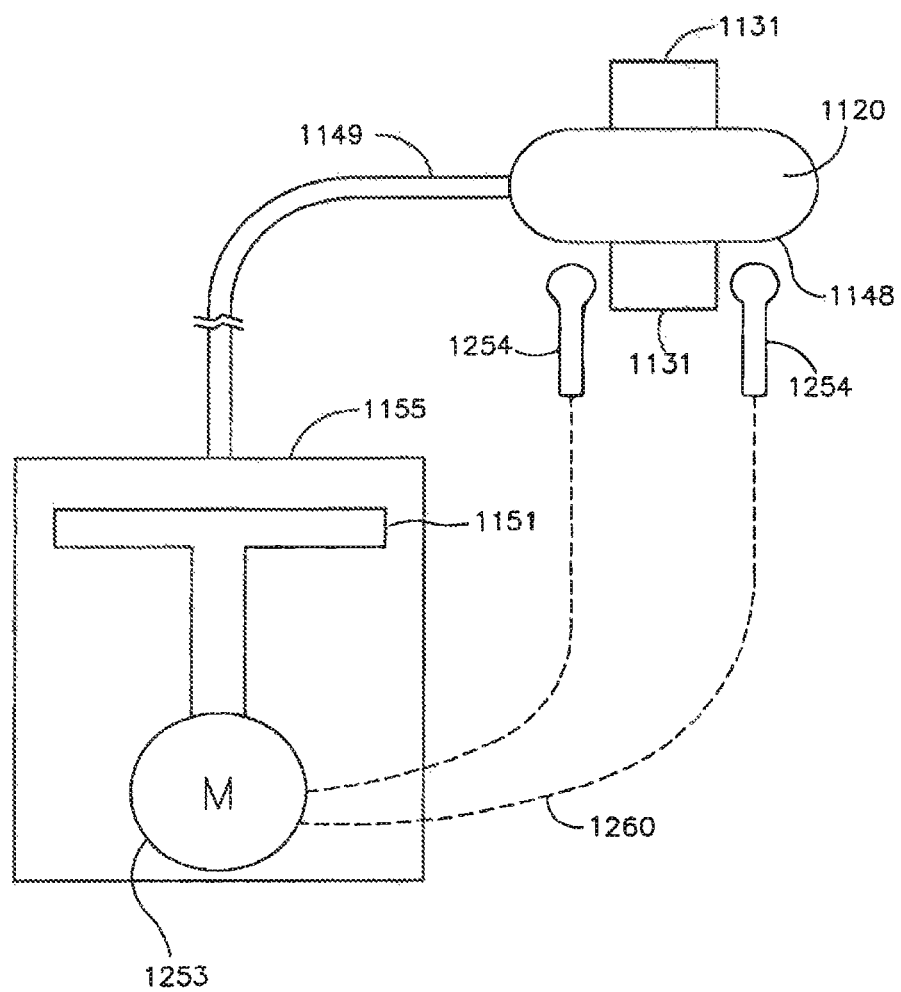
FIG. 12 is a schematic illustration of a FRM in accordance with another exemplary embodiment of the invention, which may be used, for example, in conjunction with the DPRD of FIG. 1, the shunt of FIGS. 2A-2B, or the shunt of FIG. 3.

FIG. 12 schematically illustrates a DPRD 1250 in accordance with another exemplary embodiment of the invention. DPRD 1250 may include, for example a balloon 1148 such as a non-compliant balloon containing a liquid 1120. The balloon 1148 may be placed or connected inside a ring 1131, which may include, for example, a ring similar to ring 431 and/or a frame. A tube 1149 may connect balloon 1148 to a reservoir 1155, which may include one or more pistons 1151 able to move. The piston 1151 may be moved, for example, using a motor 1153, which may include an electric motor, e.g., a step motor or other suitable motors. Motor 1153 may move, push or pull pistons 1151, thereby causing liquid 1120 to flow from balloon 1148 to reservoir 1155 or vice versa. This may change the volume of balloon 1148, thereby increasing or decreasing a size of an opening inside ring 1131, through which blood may flow from the left atrium 102 to the right atrium 103.

According to some embodiments of the present invention, the DPRD may be actively controlled, for example, by a patient or medical service provider. In one embodiment DPRD may be operated using external and/or manually provided instructions. For example, motor 1153 may operate in accordance with external and/or manually provided instructions. Additionally or alternatively, motor 1153 may operate in relation to a pressure difference between the left atrium 102 and the right atrium 103. For example, a pressure-dependent close loop 1260 may be used, incorporating one or more pressure transducers 1254. The pressure transducers 1254 may measure an absolute pressure in one or more heart chambers, for example, in left atrium 102 and/or right atrium 103, or may measure a differential pressure between two heart chambers, for example, between left atrium 102 and right atrium 103. Based upon the pressure information, motor 1153 may operate and move, push or pull the pistons 1151.

Figure 13A:
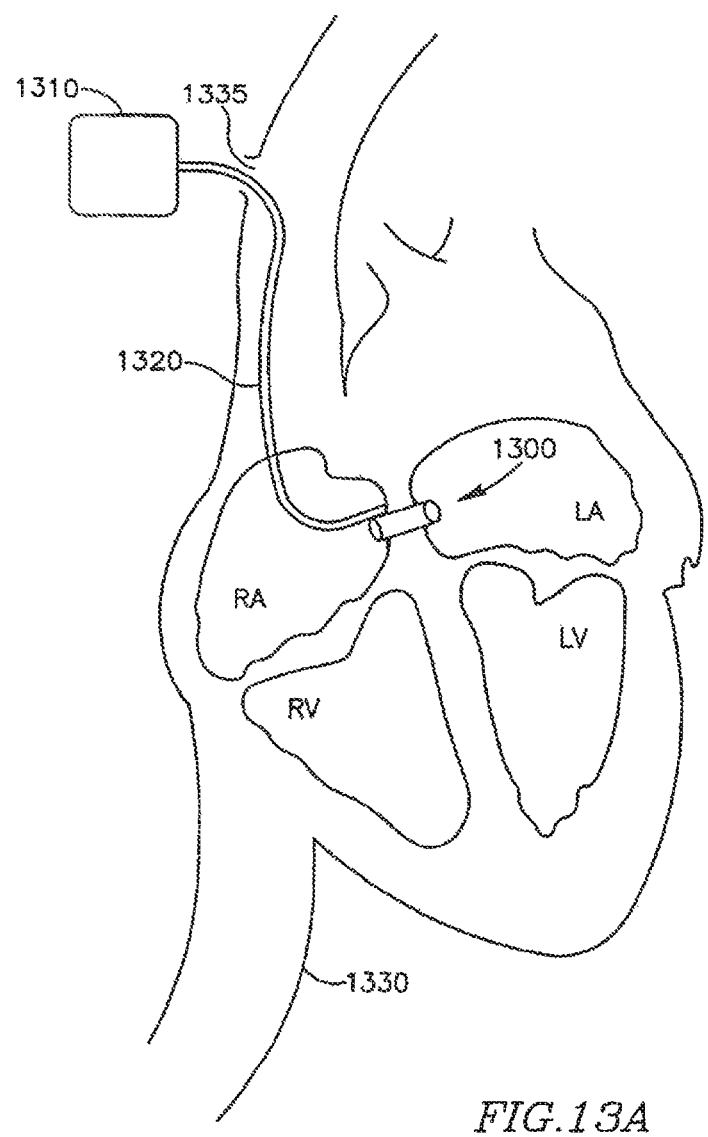
FIG. 13A is a schematic illustration of an apparatus for remotely controlling a DPRD in accordance with some embodiments of the present invention.

In other embodiments DPRD may be remotely operated using one or more of electric mechanisms, mechanical mechanisms, wireless mechanisms, pneumatic mechanisms or other suitable mechanisms. For example, a wire, line, spring, pin, cable, hook, latch, motor or magnet may be connected to the DPRD to enable the DPRD to be remotely controlled by a patient and/or medical service provider. As can be seen with reference to FIG. 13A at least one line or control lead 1320 may connect DPRD 1300 to a control mechanism 1310, for example, a control box. For example, control lead 1320 may exit vein 1330 through a puncture or hole 1335. Control mechanism 1310 may include, for example, a mechanical interface, electrical interface, pull/push wire, spring, magnet or other suitable elements or mechanisms to enable DPRD 1300 to be remotely controlled.

Control mechanism 1310 may be a micro mechanism that may be placed internally or externally, for example, it may be sown into tissue under a patient's skin, to provide external access for a medical service provider, or it may be placed internally in proximity to a location that may be accessed by a medical service provider with a minimally invasive technique.

In one embodiment DPRD 1300 may be controlled wirelessly from an external 'transmitting' unit. For example, control signals may be delivered from outside a patient's body using telemetry, localized RF radiation, localized Ultrasound radiation, external magnetic field, localized heating and other suitable means of generating signals. In such an embodiment DPRD 1300 may include a 'receiving' unit. The receiving unit may include an internal power source (e.g., a battery), or may receive its energizing power from the control signal or other transmitted signals. The receiving unit may be coupled to an external power source, for example, via an implanted plug, or may be directly connected to DPRD 1300 on a temporary basis (e.g., at the doctor's office), were the implanted plug may relay command signals and/or power to activate DPRD 1300.

Figure 13B:
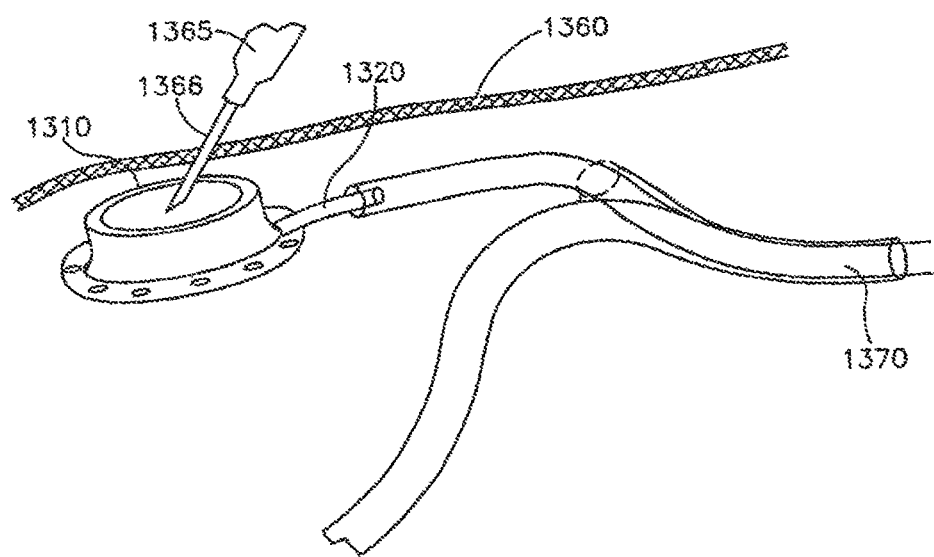
FIGS. 13B-E are schematic illustrations of mechanisms for remotely controlling a DPRD, in accordance with some embodiments of the present invention.

Reference is now made to FIG. 13B, which indicates an example of a control mechanism 1310 being positioned under the skin surface 1360. In one example control lead 1320 may be accessed by entering the patient using a conventional needle or syringe 1365, for example by making a small incision. Control lead(s) 1320 may be controlled externally or internally to enable DPRD 1300 to be controlled. In some embodiments control lead(s) 1320 may operate within a tube, for example a silicon pressurized tube 1370. Control mechanism 1310 may include a remote valve opening/closing mechanism, for example, to enable monitoring of heart pressure, monitoring of DPRD functioning etc. In one example, control mechanism 1310 may be used to monitor blood flow changes in response to valve positioning. Control mechanism 1310 may enable manual reduction of heart pressure or in blood pressure in certain chambers or the heart in the case of clinical need. Control mechanism 1310 may enable flushing or cleaning of DPRD 1300 at selected intervals, for example, by increasing internal blood pressure or fluid pressure. In other embodiments flushing or cleaning may be enabled using a flushing or cleaning fluid, for example, saline solution that may be entered into control lead 1320 at a selected pressure to cause the orifice to be cleaned or flushed. Such cleaning may help in reducing undesired growth, infections etc. associated with DPRD 1300.

Control mechanism 1310 may be coated with one or more substances to prevent thrombosis or other conditions. DPRD 1300 may include spikes, thorns or other suitable mechanisms to prevent a FRM from being in full contact with a shunt, or to ensure only minimal contact between a FRM and a shunt. Control mechanism 1310 may enable parts of DPRD 1300 to be remotely replaced, cleaned, serviced or otherwise manipulated. Control mechanism 1310 may enable a pre-configured or designed leak to be remotely opened, closed, or otherwise changed in accordance with clinical requirements. Control mechanism 1310 may enable blocking up of the DPRD's orifice or cavity, for example, by remotely placing a plug in the orifice to cease functioning of the DPRD. One or more of the above qualities may enable a health service provider to remotely control the functioning of DPRD 1300.

Figure 13C:
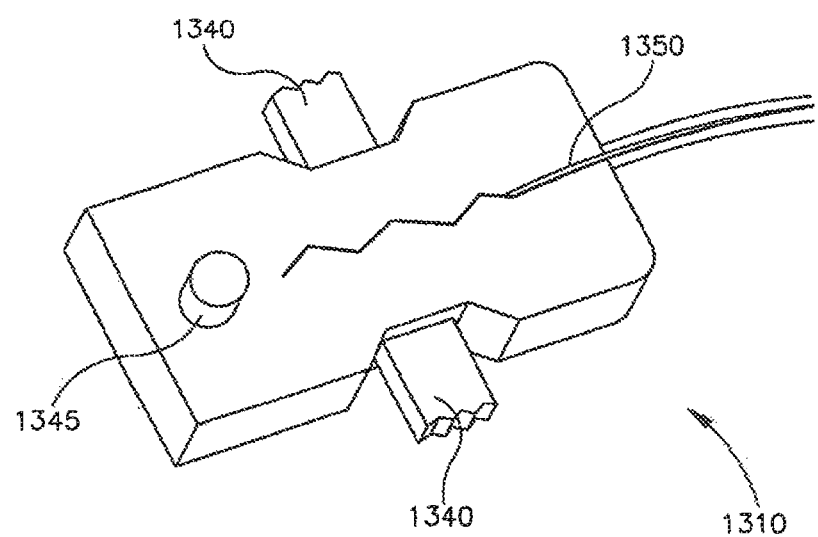

In one embodiment, as can be seen with reference to FIG. 13C, control mechanism 1310 may include one or more push knobs 1340 or other suitable controls or mechanisms that may be controlled using a finger or other suitable implement. For example, the various push knobs 1340 may be pushed individually, simultaneously and/or in various other combinations to achieve a desired effect in DPRD 1300. In one embodiment control mechanism 1310 may include, for example, one or more rods or electric conductors 1350 to help control DPRD 1300. In one embodiment control mechanism 1310 may include, for example, one or more security mechanisms 1345, for example, a locking button to help prevent non-required changes from being made to the operation of DPRD 1300. In other embodiments control mechanism 1310 may include one or more springs or other suitable control mechanisms coupled to rod 1350 and DPRD 1300.

Figure 13D:
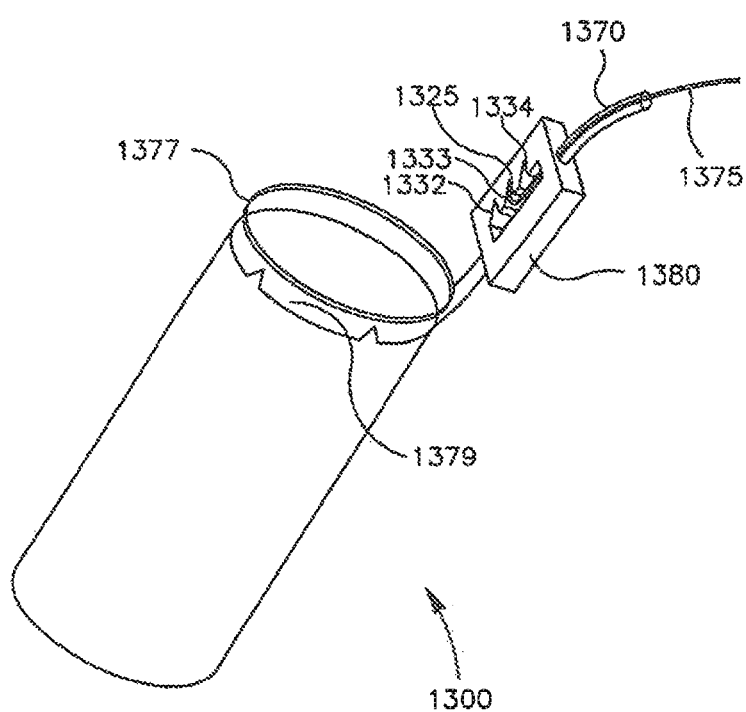

In one embodiment, as can be seen with reference to FIG. 13D, control mechanism 1310 may be used to control DPRD 1300, for example using one or more rods or wires 1375 etc., optionally operating within tube 1370. DPRD 1300 may include a cover 1377, for example, flexible or non-flexible cover, which may be left constantly ajar, for example, to form gap 1379. In one embodiment cover 1377 may be constructed from a rigid material and may be assembled or connected in a rigid manner to a locking mechanism 1380. Once cover 1377 has been set in a selected position by locking mechanism 1380, it may remain stable, for example, not being affected by blood pressure changes, until cover 1377 is re-positioned. In such a case, cover 1377 may only be adjusted by intentional and controlled actions using control mechanism 1310, for example, wires 1375 using signals, or other suitable communication links.

Locking mechanism 1380 may enable cover 1377 to be remotely set in one or more positions. Locking mechanism 1380 may include, for example, one or more of a spring, latch, lever, notch, slot, hook, slide or other suitable locking mechanism(s). For example, position #1 may be a lower position, for example where the hook 1325 fastens onto the catching mechanism 1332 as indicated; position #2 may be a medium position, for example where the hook 1325 fastens onto the catching mechanism 1333: position #3 may be a higher position for example where the hook 1325 fastens onto the catching mechanism 1334. Other settings, opening sizes, flow levels, positions and numbers of positions may be used. Control mechanism 1310 may include security features, for example, to help prevent unauthorized personnel from activating DPRD 1300 (e.g., special tools and magnets, coded sequence, password etc).

Figure 13E:
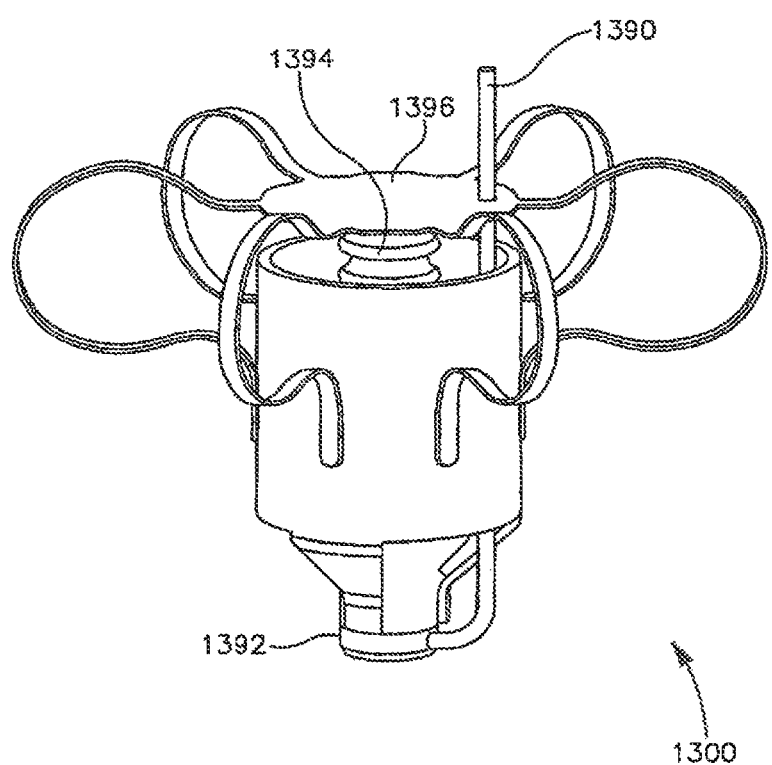

In one embodiment, as can be seen with reference to FIG. 13E, control mechanism 1310 may be used to control DPRD 1300, for example using an auxiliary hydraulic system. DPRD 1300 may be connected to the hydraulic system, for example, via one or more tubes 1390 that may help control the pressures and/or flow rates of fluids delivered through DPRD 1390. DPRD 1390 may be connected to the hydraulic system when required, or may be permanently attached to the hydraulic system. In one embodiment tubing 1390 may increase the fluid pressure in DPRD 1300, for example, to provide significant force on or inside the shunt. Tubing 1390 may additionally or alternatively be used for "maintenance", for example, by forcing liquid through the shunt, for example, via shunt base 1392, to flush, clean and/or lubricate the shunt and/or FRM 1396, and/or to release moving parts in DPRD 1300 in order to keep DPRD 1300 in a required operating condition or state. In one example, a substance (e.g., saline solution) may be injected and/or extracted to/from tubing 1390 to change the pressure at base 1392 and thereby activate piston diaphragm 1394. Piston diaphragm 1394 may be extended and/or distended thereby causing FRM 1396 to be manipulated, for example, to open and/or close FRM 1396, to allow fluid to selectively flow through DPRD 1300. Tube 1390 may be connectable to tube 1320 (see FIGS. 13A and 13B) and/or to a needle 1366 or other suitable device for penetrating a patient's skin to connect to tube 1390. In one embodiment the hydraulic mechanism may be used after deployment of DPRD 1300 in the body, for example to verify operability of DPRD 1300. In a further embodiment the hydraulic mechanism may be used when checking DPRG operability following deployment of DPRD 1300 in the body.

It will be appreciated that some embodiments of the present invention may use one or more threshold values, pre-defined parameters, conditions and/or criteria, for example, to trigger an activation or a de-activation of a shunt, a DPRD or a FRM.

Various suitable techniques for implanting a device according to an embodiment of the invention may be used. According to some embodiments, the pressure regulation device may be delivered and implanted in a patient's body using a minimally invasive procedure, for example, using percutanous delivery. In such an example, the device may be mounted on a catheter delivery system and inserted to the body via small incision. Once the device is in the correct location inside the body, it may be deployed by an operator, expanded and locked in place. A device that is delivered on a catheter may be, for example, contracted or folded into a small dimension, and the device may self-expand upon deployment. In other embodiments the pressure regulation may be delivered using invasive surgery, for example where a surgeon makes a larger opening in the body in order to achieve more direct contact with the device implantation location.

In one embodiment of the present invention, as described in embodiments in U.S. patent application Ser. No. 09/839,643, entitled "METHOD AND APPARATUS FOR REDUCING LOCALIZED CIRCULATORY SYSTEM PRESSURE" and filed on 20 Apr. 2001, in particular in FIGS. 3-5, a transseptal needle set may be advanced toward the wall of the right atrial septum. Access may be made from the femoral vein with the apparatus being advanced through the inferior vena cava and into the right atrium. Once transseptal puncture has been achieved, a guidewire may be exchanged for a needle component and then passed into the left atrium. The process of securing catheter access to the left atrium by way of a transseptal puncture is known in the art. After a transseptal sheath is positioned in the left atrium, as described above, the placement of a shunt made in accordance with embodiments of the present invention may be initiated.

The dilator and wire may subsequently be withdrawn from the sheath that may now extend from the femoral vein access point in the patient's groin to the left atrium, traversing the femoral vein, the iliac vein, the inferior vena cava, the right atrium, and the atrial septum etc. The delivery catheter may be passed through the sheath while under fluoroscopic visualization. Radiopaque markers may be provided on this catheter as well as the sheath in order to locate specific points. The delivery catheter may be carefully and slowly advanced so that the most distal portion of the left-atrial fixation element is emitted from the distal opening of the catheter and into the chamber of the left atrium. The fixation elements may be formed from a spring-like material and/or may be a super-elastic of shape-memory alloy, so that as it leaves the constraint provided by the inner area of the delivery catheter, it reforms into its pre-con figured fully formed shape. The assembly of the sheath and the delivery catheter may then slowly be retracted en bloc so as to withdraw the fixation elements towards the atrial septum. The physician may stop this retraction when it becomes apparent by fluoroscopic visualization as well as by tactile feedback that the fixation element has become seated against the atrial septum. At that point, the sheath alone may be retracted, uncovering the shunt and positioning it within the opening that has been created within the atrial septum. The sheath may then be further retracted, allowing the right-atrial fixation element to reform into its fully formed shape. The entire shunt assembly or DPRD may then be detached from the delivery catheter system. The DPRD may be controlled within the delivery catheter by means of long controller wire that has independent translational control within the catheter area. This attachment may be formed by any conventional method, e.g., a solder or adhesive or the like that may mechanically detach at a prescribed tension level, that level being exceeded by the physician at this point in the procedure by firmly retracting the controller wire. Other methods of deployment of DPRD and/or FRM may be used.

Figure 14:
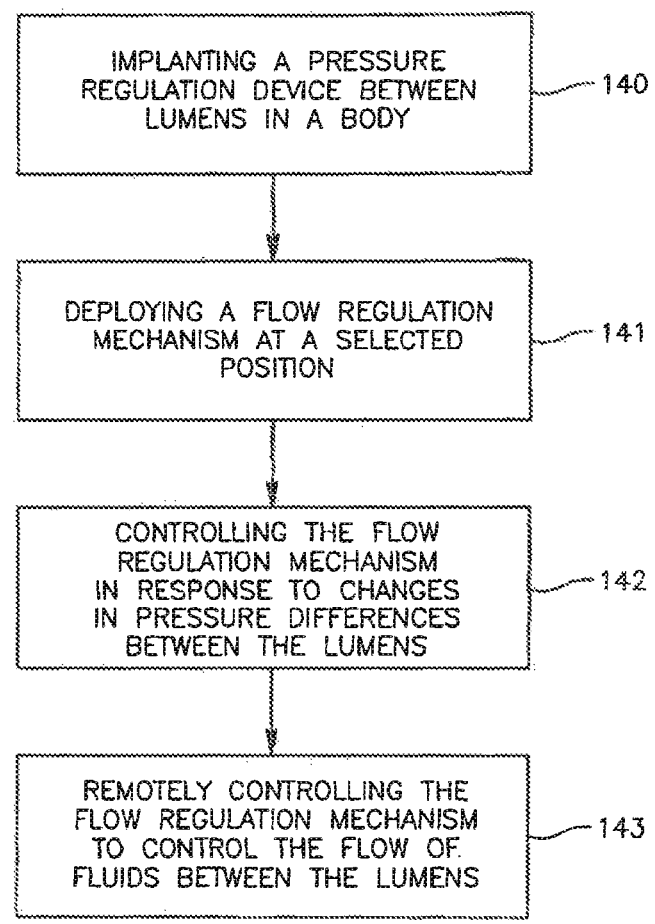
FIG. 14 is a flow chart illustrating a method of controlling pressure, for example, blood pressure in a heart, according to some embodiments of the present invention.

Reference is now made to FIG. 14, which illustrates a method of delivering a DPRD and/or a FRM into a body area, for example, the septum of the heart between the left and right atrium, according to some embodiments of the present invention. Implantation of a device in the septum may involve one or more of the following processes: a) identifying the precise site for implantation; b) aiming the device toward the selected site; and c) ensuring accuracy and integrity of the implantation. The ideal implantation position may be chosen, for example, by a medical professional, for example, by imaging the septum and analyzing the septum anatomy (e.g., by TEE). The aiming may include identifying the precise device delivery tool location using known tools for 'mapping' the septum site. Markers may be added to the delivery tools and devices (e.g., gold markers). Once the position has been identified and the device has been deployed, the medical professional may check and test the device installation, optionally before full retrieval of the delivery system. For example, the medical professional may use direct contact such as physically challenging or pulling the entire device (e.g., by pulling gently on the device to ensure proper anchoring). The anchoring may be tested by non-contact means (e.g., using electromagnetic imaging, Echo, x-ray, angiography with contrast material etc.).

At block 140 a DPRD may be implanted between two or more chambers, lumens, organs, regions, zones etc. in a body, for example, using a catheter. At block 141 a FRM may be deployed in a selected setting or position, for example, to enable a continuous flow of fluid between two or more lumens, and to be selectively activated or de-activated in accordance with changes in pressure differences between the lumens. At block 142 the FRM may be controlled (e.g., passively) in response to changes in pressure differences between the lumens, for example, FRM may be further opened and/or closed in response to a pressure change. Optionally, at block 143 the DPRD and/or FRM may be remotely controlled to help control the flow of fluids between the lumens. In some embodiments the remote control of the DPRD and/or FRM may enable cleaning the DPRD and/or FRM, disabling the DPRD and/or FRM, changing elements of the DPRD and/or FRM etc. Any combination of the above steps may be implemented. Further, other steps or series of steps may be used.

The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

What is claimed:

1. A device for implantation within an atrial septum of a patient's heart to treat a heart condition, the device comprising:
a shunt comprising flexible material and configured to transition between a collapsed delivery state and an expanded deployed state, the shunt further configured to engage an opening in the atrial septum in the expanded deployed state and defining a continuous opening in the atrial septum to permit passage of blood through the atrial septum via the shunt, the continuous opening having an adjustable cross-sectional area such that blood flow across the atrial septum through the continuous opening of the shunt is adjustable.

2. The device of claim 1, wherein the shunt is configured to permit passage of blood through the atrial septum to unload an excessive filling pressure of a left ventricle in a patient with congestive heart failure.

3. The device of claim 1, wherein the shunt comprises a flexible metal.

4. The device of claim 3, wherein the flexible metal comprises Nitinol.

5. The device of claim 1, wherein the shunt comprises a shape-memory material.

6. The device of claim 1, wherein the shunt is configured to self-expand from the collapsed delivery state to the expanded deployed state.

7. The device of claim 1, wherein the shunt is configured to protrude into at least one of a right atrium and a left atrium of the patient in the expanded deployed state.

8. The device of claim 1, further comprising a flexible membrane disposed within the shunt to define the continuous opening in the atrial septum.

9. The device of claim 8, further comprising a spring configured to expand and contract the flexible membrane responsive to changes in blood pressure differential across the atrial septum, thereby changing the cross-sectional area of the continuous opening.

10. The device of claim 9, wherein the spring comprises a predetermined spring tension to respond in a controlled manner to changes in blood pressure differential across the atrial septum.

11. The device of claim 1, wherein the rate of blood flow through the shunt, cross-sectional area of the continuous opening, and blood pressure differential across the atrial septum have a relationship dependent on a predetermined pressure differential threshold.

12. The device of claim 1, further comprising a coating to increase bio-compatibility.

13. The device of claim 1, further comprising an anchor for retaining the shunt in the opening in the atrial septum in the expanded deployed state.

14. A method for treating a heart condition, the method comprising:
delivering a shunt within a puncture of an atrial septum of a patient's heart in a collapsed delivery state;
transitioning the shunt from the collapsed delivery state to an expanded deployed state within the atrial septum, the shunt defining a continuous opening within the atrial septum in the expanded deployed state; and
permitting blood flow across the atrial septum via the continuous opening of the shunt,
wherein a cross-sectional area of the continuous opening is adjustable such that blood flow across the atrial septum through the continuous opening of the shunt is adjustable.

15. The method of claim 14, wherein delivering the shunt within the puncture of the atrial septum comprises delivering the shunt in a minimally invasive procedure.

16. The method of claim 14, wherein delivering the shunt within the puncture of the atrial septum comprises:
advancing a guidewire and dilator within a puncture of an atrial septum of a patient's heart;
advancing a sheath over the guidewire and dilator; and
removing the dilator from the patient's body.

17. The method of claim 14, wherein transitioning the shunt from the collapsed delivery state to the expanded deployed state within the atrial septum comprises:
advancing a delivery catheter mounted to the shunt in the collapsed delivery state through a sheath positioned within the puncture of the atrial septum until a first end of the shunt self-expands within a first atrium of the patient's heart; and
retracting the sheath relative to the atrial septum until a second end of the shunt self-expands within a second atrium of the patient's heart.

18. The method of claim 17, further comprising retracting the delivery catheter and retracting the sheath relative to the atrial septum until the first end is seated against the atrial septum prior to retracting the sheath until the second end of the shunt self-expands within the second atrium.

19. The method of claim 14, further comprising creating the puncture within the atrial septum of a patient's heart.

20. The method of claim 17, further comprising removing the sheath and the delivery catheter from the patient's body.

21. The method of claim 17, further comprising, after the shunt self-expands within the first atrium, retracting the delivery catheter relative to the shunt.

22. The method of claim 17, further comprising, after the first end of the shunt self-expands within the first atrium but prior to retracting the sheath until the second end of the shunt self-expands within the second atrium, retracting the delivery catheter and retracting the sheath relative to the atrial septum.

23. The method of claim 17, further comprising controlling delivery of the shunt using a control wire.

24. The method of claim 16, further comprising, after transitioning the shunt from the collapsed delivery state to the expanded deployed state within the atrial septum, removing the guidewire from the patient's body.

25. The method of claim 14, wherein permitting the blood flow across the atrial septum via the continuous opening of the shunt is configured to treat heart failure.

26. The method of claim 14, wherein permitting the blood flow across the atrial septum via the continuous opening of the shunt is configured to treat pulmonary hypertension.

27. The method of claim 14, wherein the shunt comprises a flexible metal.

28. The method of claim 27, wherein the flexible metal comprises Nitinol.

29. The method of claim 14, wherein the shunt comprises a shape-memory material.

30. The method of claim 29, wherein the shunt further comprises a super elastic alloy.

31. The device of claim 5, wherein the shunt further comprises a super elastic alloy.

32. The device of claim 1, wherein the shunt is configured to permit passage of blood through the atrial septum to treat pulmonary hypertension.

33. The device of claim 1, wherein the cross-sectional area of the continuous opening is from 3.5 mm$^2$ to 24 mm$^2$ for blood flow through the shunt.

34. The device of claim 1, wherein the shunt is configured to provide enhanced blood flow across the atrial septum via the continuous opening when the interatrial pressure gradient ranges from greater than a threshold between 0 and 25 mmHg.

35. The device of claim 1, wherein the cross-sectional area of the continuous opening is dependent on blood pressure differential across the atrial septum such that blood flow through the shunt changes responsive to change in the blood pressure differential across the atrial septum.

36. The device of claim 1, wherein the shunt further comprises a flow regulating mechanism for adjusting the cross-sectional area of the continuous opening of the shunt.

* * * * *